United States Patent [19]

Taniguchi et al.

[11] Patent Number: 5,652,095

[45] Date of Patent: Jul. 29, 1997

[54] INTERFERON REGULATORY FACTORS 1 AND 2 IN THE DIAGNOSIS OF TUMORIGENICITY

[75] Inventors: Tadatsugu Taniguchi, Mihogaoka 19 A-207, Ibaraki-shi, Osaka 567, Japan; Cheryl L. Willman, Albuquerque, N. Mex.; Maria G. Pallavicini, Livermore, Calif.; Hisashi Harada; Nobuyuki Tanaka, both of Osaka, Japan

[73] Assignees: The Regents of the University of California, Oakland, Calif.; The University of New Mexico, Albuquerque, N. Mex.; Tadatsugu Taniguchi, Osaka, Japan

[21] Appl. No.: 126,966

[22] Filed: Sep. 24, 1993

Related U.S. Application Data

[63] Continuation-in-part of Ser. No. 995,594, Dec. 22, 1992, abandoned, which is a continuation-in-part of Ser. No. 950,574, Sep. 24, 1992, abandoned.

[30] Foreign Application Priority Data

Sep. 24, 1993 [WO] WIPO ............... PCT/US93/09185

[51] Int. Cl.⁶ ............................................. C12Q 1/68
[52] U.S. Cl. ............................................. 435/6
[58] Field of Search .................. 435/6, 77, 78; 436/813

[56] References Cited

U.S. PATENT DOCUMENTS 4,683,195  7/1987  Mullis et al. ......................... 435/6

OTHER PUBLICATIONS

Harada et al, Science 259:971–974 (1993).
Willman et al, Science 259:968–970 (1993).
Au et al., "Distinct activation of murine interferon–α promotor region by IRF–1/SFG–2 and virus infection", *Nucl. Acids Research* 20(11): 2877–2884 (1992).
Fujita et al., "Induction of endogenous IFN–α and IFN–β genes by a regulatory transcription factor, IRF–1", *Nature* 337:270–272 (Jan. 1989).
Fujita et al., "Evidence for a nuclear factor(s), IRF–1, mediating induction and silencing properties to human IFN–β gene regulatory elements", *EMBO J* 7(11): 3397–3405 (1988).
Harada et al., "Structurally similar but functionally distinct factors, IRF–1 and IRF–2, bind to the same regulatory elements of IFN and IFN–inducible genes", *Cell* 58: 729–739 (Aug. 25, 1989).
Harada, Hisashi et al., "Absence of the type I IFN system in EC cells: Transcriptional activator (IRF–1) and repressor (IRF–2) are developmentally regulated", *Cell* 63: 303–312 (Oct. 19, 1990).
Itoh, S. et al., "Assignment of the Human Interferon Regulatory Factor-1 (IRF1) Gene to Chromosome 5q23–q31", *Genomics* 10:1097–1099 (1991).
Le Beau et al., "Interleukin–4 and interleukin–5 map to human chromosome 5 in a region encoding growth factors and receptors and are deleted in myeloid leukemias with a del (5q)", *Blood* 73 (3): 647–650 (Feb. 15, 1989).

(List continued on next page.)

*Primary Examiner*—W. Gary Jones
*Assistant Examiner*—Eggerton Campbell
*Attorney, Agent, or Firm*—Sterne, Kessler, Goldstein & Fox

[57] ABSTRACT

The present invention relates, in general, to a method of diagnosing tumorigenic mammalian cells or the propensity of a mammalian cell to become tumorigenetic. Additionally, the present invention relates to a cloned cDNA or genomic DNA for reducing the propensity of a cell to become tumorigenic or suppressing tumorigenic phenotype of a cell; a method of reducing the propensity of a cell to become tumorigenic or suppressing the tumorigenic phenotype of a cell; a method of treating a patient suffering from or predisposed to subsequent cancer development; and a method of diagnosing tumorigenic tissue of a human or tissue predisposed to become tumorigenic.

15 Claims, 13 Drawing Sheets

OTHER PUBLICATIONS

Maruyama et al., "Sequence of a cDNA coding for human IRF-1", *Nucl. Acids Res.* 17(8):3292 (1989).

Miyamoto et al., "Regulated expression of a gene encoding a nuclear factor, IRF-1, that specifically binds to IFN-β gene regulatory elements", *Cell* 54: 903–913 (Sep. 9, 1988).

Näf et al., "Multimerization of AAGTGA and GAAAGT generates sequences that mediate virus inductibility by mimicking an interferon promoter element", *Proc. Natl. Acad. Sci. USA* 88:1369–1373 (Feb. 1991).

Pederson, B. and Jensen, I.M., "Clinical and prognostic implications of chromosome 5q deletions: 96 high resolution studied patients", *Leukemia* 5(7) :566–573 (Jul. 1991).

Reis et al., "Critical role of a common transcription factor, IRF-1, in the regulation of IFN-β and IFN-inducible genes", *EMBO J.* 11(1) :185–193 (1992).

Stark, G.R. and Kerr, I.M., "Interferon-dependent signaling pathways: DNA elements, transcription factors, mutations, and effects of viral proteins", *J. Interferon Research* 12:147–151 (1992).

Watanabe et al., "Activation of IFN-β element by IRF-1 requires a post-translational event in addition to IRF-1 synthesis", *Nucl. Acid Res.* 19(16) :4421–4428 (1991).

Yamada et al., "Specific depletion of the B-cell population induced by aberrant expression of human interferon regulatory factor 1 gene in transgenic mice", *Proc. Natl. Acad. Sci. USA* 88:532–536 (Jan. 1991).

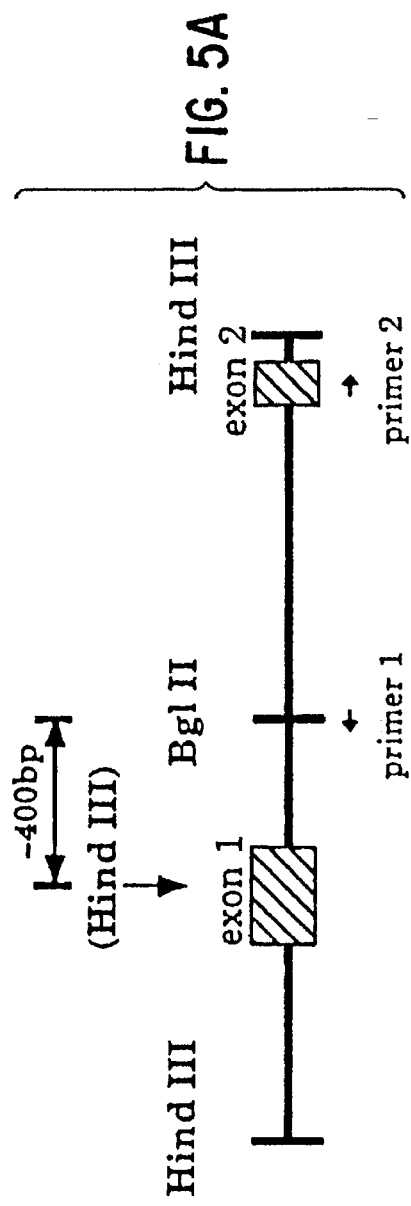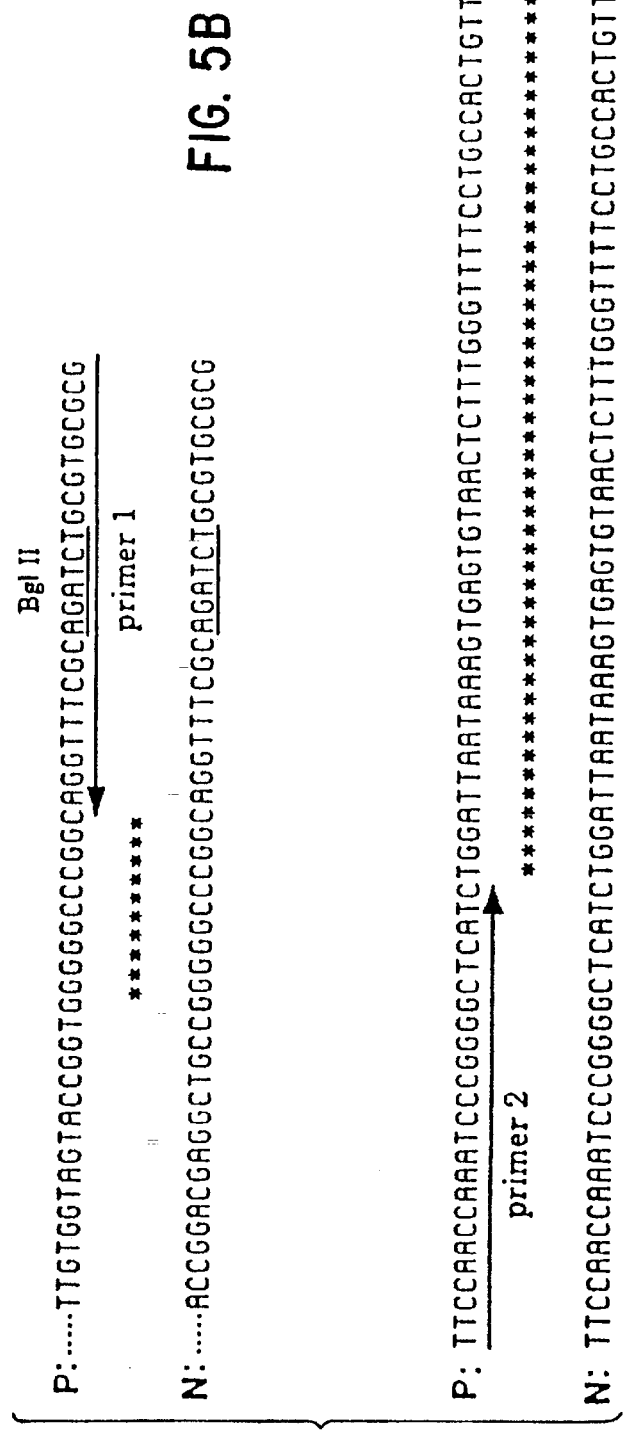
FIG. 5A
FIG. 5B

INTERFERON REGULATORY FACTORS 1 AND 2 IN THE DIAGNOSIS OF TUMORIGENICITY

BACKGROUND OF THE INVENTION

This application is a continuation-in-part of application Ser. No. 07/995,594, filed Dec. 22, 1992, abandoned which is a continuation-in-part of application Ser. No. 07/950,574, filed Sep. 24, 1992, abandoned claiming priority to PCT/US93/09185, filed on Sep. 24, 1993, the contents of each of which are fully incorporated herein by reference.

This invention was made with government support under Grant No. AI 27909 awarded by the National Institutes of Health. The government has certain rights in the invention.

FIELD OF THE INVENTION

The present invention relates, in general, to a method of diagnosing tumorigenic mammalian cells or the propensity of a mammalian cell to become tumorigenetic. Additionally, the present invention relates to a cloned cDNA or genomic DNA for reducing the propensity of a cell to become tumorigenic or suppressing tumorigenic phenotype of a cell; a method of reducing the propensity of a cell to become tumorigenic or suppressing the tumorigenic phenotype of a cell; a method of treating a patient suffering from or predisposed to subsequent cancer development; and a method of diagnosing tumorigenic tissue of a human or tissue predisposed to become tumorigenic.

BACKGROUND INFORMATION

1. Interferons and Interferon Regulatory Factors 1 and 2

Interferons (IFNs) belong to a family of pleiotropic cytokines which were originally identified based on their anti-viral properties. A variety of tissues generate type I IFNs, i.e. IFN-$\alpha$s and IFN-$\beta$, upon viral infection and the secreted IFNs subsequently exert their anti-viral activity on target cells by inducing a set of genes, the IFN-inducible genes. Recently, much attention has been focused on the role of IFNs in cell growth and differentiation, and it has been shown that IFNs exhibit anti-proliferative effects on many normal and transformed cells (reviewed by Weissmann and Weber, *Prog. Nucleic Acid Res. Mol. Biol.* 33: 251–300 (1986); Pestka et al., *Annu. Rev. Biochem.* 56: 727–777 (1987); De Maeyer and De Maeyer-Guignard, *Interferons and Other Regulatory Cytokines*, New York, John Wiley and Sons (1988); Taniguchi, *Annu. Rev. Immunol.* 6: 439–464 (1988); Vilcek, "Interferons etc.," *Handbook of Experimental Pharmacology*, Sporn and Roberts, eds., Berlin, Springer-Verlag, pp. 3–38 (1990); Sen and Lengyel, *J. Biol. Chem.* 267: 5017–5020 (1992)). In addition, a number of studies have demonstrated that IFNs and growth stimulatory factors act in a mutually antagonistic manner; IFNs have been shown to block growth factor-stimulated cell cycle transitions, while certain growth factors have been shown to reverse the anti-proliferative effects of IFNs. Furthermore, IFNs are induced by a number of growth factors, suggesting a physiological role for IFNs in a feedback mechanism that regulates cell growth. Hence these observations have lent support to the prevailing notion that IFNs are "negative growth factors" (reviewed by Clements and McNurian, *Biochem. J.* 226: 345–360 (1985); Tamm et al., *Interferon* 9, I. Gresser, ed., California, Academic Press, pp. 14–74 (1987); De Maeyer and De Maeyer-Guignard, ibid. (1988); Gresser, *Acta Oncologica* 28: 347–353 (1989); Vilcek, ibid. (1990)). In this context, it is interesting to note that type I IFN genes are frequently deleted in some types of malignancies (Diaz et al., *Proc. Natl. Acad. Sci. USA* 85: 5259–5263 (1988); Miyakoshi et al., *Cancer Res.* 50: 278–283 (1990)). However, little is known about the mechanistic aspects of these anti-proliferative effects of IFNs.

During studies on the regulatory mechanism(s) of human IFN-$\beta$ gene, two novel DNA-binding factors, Interferon Regulatory Factor-1 (IRF-1) and -2 (IRF-2) were identified (Fujita et al., *EMBO J.* 7: 3397–3405 (1988); Miyamoto et al., *Cell* 54: 903–913 (1988); Harada et al., *Cell* 58: 729–739 (1989)). The amino acid sequences for human and mouse IRF-1 and mouse IRF-2 as well as the DNA sequences coding therefore are also disclosed in the U.S. patent application Ser. No. 07/397,967, filed Aug. 24, 1989. These two factors are structurally related, particularly in the N-terminal regions which confer DNA binding specificity. In fact, both factors bind to the same DNA sequence elements found within the promoters of IFN-$\alpha$s, IFN-$\beta$ and many IFN-inducible genes (Harada et al., ibid. (1989)). A series of gene transfection studies have demonstrated that IRF-1 functions as a critical activator for IFN and IFN-inducible genes, Whereas IRF-2 represses the IRF-1 effect (Fujita et al., *Nature* 337: 270–272 (1989); Harada et al., *Cell* 63: 303–312 (1990); Näf et al., *Proc. Natl. Acad. Sci. USA* 88: 1369–1373 (1991); Au et al., *Nucl. Acids Res.* 20: 2877–2884 (1992); Reis et al., *EMBO J.* 11: 185–193 (1992); Stark and Kerr, *J. Interferon R.* 12: 147–151 (1992)). In the context of the IFN-mediated cellular response, it is interesting that expression of IRF-1 gene itself is IFN-inducible. The IRF-2 gene is also induced in IFN-stimulated cells, but this induction occurs only following IRF-1 gene induction (Harada et at., ibid. (1989)). Moreover, previous studies have revealed that IRF-1 and IRF-2 differ in terms of their stability; the former has a short half-life (about 30 min.), whereas the latter is relatively stable (half-life; about 8 hrs) in INF-treated or virus-infected cells. In growing cells, IRF-2 levels are higher than those of IRF-1, but the IRF-1/IRF-2 ratio increases following stimulation by IFNs or viruses (Watanabe et at., *Nucl. Acid Res.* 19: 4421–4428 (1991)). Therefore, a transient increase in the IRF-1/IRF-2 ratio may be a critical event in the regulation of cell growth by IFNs. Consistent with this notion are the findings that transgenic mice carrying the human IRF-1 gene linked to the human immunoglobulin gene enhancer are deficient in developing B lymphocytes (Yamada et al., *Proc. Natl. Acad. Sci. USA* 88: 532–536 (1991)).

2. Tumor Suppressor Genes

Human tumorigenesis is a multistep process resulting from the progressive acquisition of mutations at multiple genetic loci that regulate cell growth, differentiation, and metastasis. In the best-studied human tumor models, "gain-of-function" mutations found in dominantly-acting proto-oncogenes are accompanied by "loss-of-function" mutations in tumor suppressor genes. Although numerous proto-oncogenes were initially identified and characterized, recent studies have identified several tumor suppressor genes whose mutation or deletion appears to be critical for the development of human tumors, including RB, p53, and WT1 (reviewed in Marshall, *Cell* 64: 313–326 (1991)), as well as APC (Groden et al., *Cell* 66: 589–600 (1991); Kinzler et al., *Science* 253: 661–664 (1991)), and NF1 (Xu et al., *Cell* 62: 599–608 (1990); Marshall, ibid. (1991); Li et al., *Cell* 69: 275–281 (1992)). The loss of heterozygosity at additional genetic loci (Ponder, *Nature* 335: 400–402 (1988); Marshall, ibid. (1991)) and the recurrent deletion of specific chromosomal regions in human tumors have supported the view that many more candidate tumor suppressor genes remain to be identified.

An interstitial deletion of the long arm of chromosome 5(del(5q); the "5q-" eytogenetic abnormality) or loss of a whole chromosome 5(-5 or monosomy 5) are among the most frequent recurrent cytogenetic abnormalities in human leukemia and the preleukemic myelodysplastic syndromes (myelodysplasia; MDS). Del(5q)or monosomy 5 is found in 30% of patients with MDS, in 50% of patients with secondary or therapy-induced acute myelogenous leukemia (AML), and in 15% and 2% of patients with de novo AML and de novo acute lymphocytic leukemia (ALL), respectively (Van den Berghe et al., Nature 251: 437 (1974), Cancer Genet. Cytogenet. 17: 189–255 (1985); Fourth International Workshop on Chromosomes in Leukemia, (1982); Le Beau et al., J. Clin. Oncol. 4: 325–345 (1986); Nimer and Golde, Blood 70: 1705–1712 (1987); Kerim et al. Leukemia 4: 12–15 (1990); Pederson-Bjergaard et al., Blood 76: 1083–1091 (1990)). The del(5q) was first described as the hallmark of a unique myelodysplastic syndrome (the "5q-Syndrome") occurring predominantly in elderly females that is characterized by refractory anemia, thrombocytosis, and abnormal megakaryocytes (Van den Berghe et al., ibid. (1974)). Females with this syndrome usually have an indolent clinical course; the affected myeloid stem cell clone appears to have a slow capacity for expansion, acquires additional cytogenetic abnormalities only infrequently, and transforms to AML in only 10–20% of cases (Van den Berghe et al., ibid. (1985); Dewald et al., Blood 66: 189–197 (1985); Nimer and Gold, ibid. (1987)). In contrast, patients who present with de novo or secondary AML with del(5q) usually have additional cytogenetic abnormalities at presentation and a very poor prognosis (Rowly et al., Blood 58: 759–767 (1981); Fourth International Workshop on Chromosomes in Leukemia (1982); Le Beau et al., ibid. (1986); Samuels et al., Leukemia 2: 79–83 (1988)). In AML, the presence of a del(5q)/-5 has also been associated with occupational exposure to carcinogens (Mitelman et al., Blood 52: 1229–1273 (1978); Golomb et at., Blood 60: 404–411 (1982)) or with previous exposure to alkylating agent chemotherapy or radiotherapy for the treatment of various malignancies (Le Beau et al., ibid. (1986)). A series of studies have revealed that the smallest commonly deleted segment of the del(5q), the so called "critical" region, lies in band 5q31 (Le Beau et al., Blood 73: 647–650 (1989); Pederson and Jensen, Leukemia 5: 566–573 (1991)). Rare de novo AMLs with translocations involving 5q31 have also been described (Fourth International Workshop on Chromosomes in Leukemia, 1982). These findings suggest that the causative gene(s) lies in 5q31 and that deletion of this gene(s) may be central to the pathogenesis of leukemia and MDS. Numerous candidate genes have been mapped to the 5q31 region, including the hematopoietic growth factors and interleukins IL-3, IL-4, IL-5, IL-9, and GM-CSF, and, the EGR-1 transcription factor (Huebner et at., Science 230: 1282–1285 (1985); Le Beau et al., Science 231: 984–987 (1986) and ibid. (1989); Sutherland et al., Blood, 71: 1150–1152 (1988); Warrington et at., Genomics 13: 803–808 (1992)). However, none of these genes currently appear to fulfill the requirements expected of a candidate tumor suppressor gene. Loss of one IL-3, IL-4, IL-5, and GM-CSF allele has been frequently, though not consistently, reported in leukemia and MDS patients with del(5q) (Le Beau et at., ibid. (1986), Proc. Natl. Acad. Sci. USA 84: 5913–5917 (1987), ibid. (1989); Nimer and Golde, ibid. (1987)). However, no reduction to homozygosity, structural rearrangements, or mutations in the residual alleles have been discovered (see Nimer and Golde, ibid. (1987)). Recent studies of EGR-1 in del(5q) patients have yielded similar negative findings (G. Gilliland et at., Harvard University, personal communication). Thus, a candidate tumor suppressor gene remained to be identified in this region.

SUMMARY OF THE INVENTION

It is a general object of this invention to provide a method of diagnosing tumorigenic cells or the propensity of a cell to become tumorigenetic.

It is a specific object of this invention to provide a method of diagnosing tumorigenic mammalian cells or the propensity of a mammalian cell to become tumorigenetic.

It is a specific object of this invention to provide a cloned cDNA or genomic DNA for reducing the propensity of a cell to become tumorigenic or suppressing tumorigenic phenotype of a cell.

It is a further object of the invention to provide a method of reducing the propensity of a cell to become tumorigenic or suppressing the tumorigenic phenotype of a cell.

It is another object of the invention to provide a method of treating a patient suffering from or predisposed to subsequent cancer development.

It is a further object of the invention to provide a method of diagnosing tumorigenic tissue of a human or tissue predisposed to become tumorigenic.

Further objects and advantages of the present invention will be clear from the description that follows.

DESCRIPTION OF THE FIGURES

FIG. 3 shows the results of dual color fluorescence in-situ hybridization in interphase nuclei using an IRF-1 probe (arrow 1) and 5q22 (arrow 2) with:

Figure 1A:
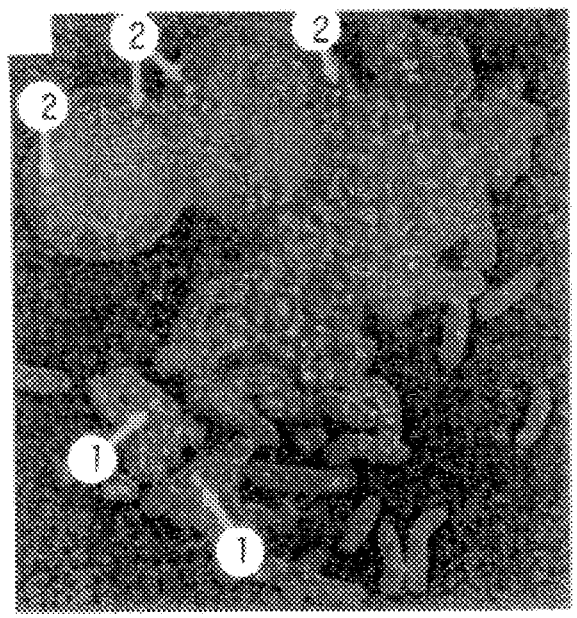
In FIG. 1A propidium iodide-stained metaphase chromosomes from normal lymphocytes are shown to be hybridized with an IRF-1 genomic clone. The IRF-1 probe is specifically hybridized to sequences on chromosome 5q (arrows 1). Two IRF-1 hybridization domains (arrows 2) are also detected in interphase nuclei.

(A) a normal lymphocyte with 2 5q22 and 2 IRF-1 alleles;

(B) a leukemic cell (representative of Sample 12, Table 1) in S phase with 4 5q22 and only 2 IRF-1 domains, indicating deletion of 1 IRF-1 allele;

(C) a leukemic cell (Sample 7, Table 1) with only 15q22 and 1 IRF-1 domain due to del(5) (q11q33).

FIG. 4 depicts the characterization of a structural rearrangement of the IRF-1 gene in a case of acute leukemia (Table 1, Sample 10), wherein (A) is a map of the human IRF-1 gene and enlargement of the HindIII region containing exons 1 and 2. The upper panel shows the exon map of the human IRF-1 gene; positions of the exons are indicated by filled boxes. The lower panel enlarges the HindIII region containing exons 1 and 2. The positions of the exons are indicated by hatched boxes and the probes used in Southern blot analysis are indicated as probe 1 and probe 2. Restriction enzyme sites: H, HindIII; Ba, BamHI; Bg, BglII. (Ba) indicates a polymorphic BamHI site.

(B,C,D) are Southern blot analysis of genomic DNA from normal DNA (N) and Patient Sample 10 (P). An identically prepared filter was hybridized with each of the following probes: the IRF-1 cDNA (FIG. 4B) 2.0 kb XhoII fragment from pHIRF31; see Experimental Procedures), probe 1, (FIG. 4C a 1.0 kb HindIII-BglII fragment as noted in FIG. 4A) and probe 2 (FIG. 4D; a 1.0 kb BglII-HindIII fragment as noted in FIG. 4A). Arrows indicate deletions and novel bands appearing in the leukemic sample (P) relative to normal (N) DNA. Normal DNA means DNA from a healthy non-leukemic unrelated individual.

FIG. 5 depicts the cloning and sequencing of breakpoints within the IRF-1 gene using inverse PCR, (A) is a map of the 1.9 kb HindIII-HindIII region of the IRF-1 gene encompassing exons 1 and 2 and intron 1. The novel HindIII site in the leukemic sample (Sample 10) and resultant 400 bp HindIII fragment are indicated by (HindIII) above the map. The primers and orientations used for inverse PCR are also indicated.

(B) is a sequence of the cloned PCR product derived from the leukemic sample (P; Sample 10) and from normal DNA (N). Identical sequences in the leukemic and normal DNA are indicated by a*. The sequence of the leukemic sample is shown to diverge 10 nucleotides after primer 1 in intron 1 SEQ ID NOS. 1-4.

FIG. 6 shows the oscillation of IRF-1 mRNA expression during the cell cycle.

(A) shows the kinetics of thymidine incorporation by serum stimulation. The maximum level of $^3$H-thymidine incorporation achieved during the time course ($1.3 \times 10^5$ cpm/$2 \times 10^4$ cells at 20 hours) is taken as 100%.

(B) shows the expression of IRF-1 and IRF-2 mRNAs during serum-induced growth. NIH3T3 cells were initially arrested by serum starvation and subsequently induced by serum addition. The upper panel shows the result of S1 mapping analysis. At the indicated times, total RNA was isolated and subjected to the analysis. The arrows indicate the positions of the protected IRF-1 and IRF-2 probes. Lane M corresponds to $^{32}$P-labelled HaeIII-digested pBR322 DNA fragments. The lower panel shows the mRNA copy numbers of IRF-1 and IRF-2 obtained from the upper panel as calculated by densitometric analysis. The profiles are indicated for IRF-1 (open circles) and IRF-2 (closed circles).

(C) shows the expression of IRF-1 protein during the serum-induced growth. NIH3T3cells were growth-arrested and stimulated as in (B).

FIG. 7 illustrates the overexpression of IRF-2 in NIH3T3 cells.

(A) shows the Northern blot analysis in which the expression of IRF-2 mRNA was followed.

(B) shows the gel shift analysis of IRF-2 activity transfected NIH3T3 cells. Arrowheads indicate the position of IRF-2-DNA complexes. Faster migrating band probably represent the breakdown product of IRF-2 bound to the DNA probe (See also FIG. 8B).

(C) shows the growth curves of control cell lines and of cell lines overexpressing IRF-2. Growth profiles are indicated for C-2 (open circles), C-3 (open boxes), 2-1 (filled circles), 2-5 (filled boxes), and 2-7 (filled triangles).

FIG. 8 illustrates the reversal of the IRF-2-induced transformation by IRF-1.

(A) shows the expression of human IRF-1 mRNA in hygromycin-resistant clones which were mock-induced (lanes 1 to 7) or induced by NDV (Newcastle Disease Virus) (lanes 8 to 12). The cell lines were as follows: lanes 1 and 8, cell line 2-1-1; lanes 2 and 9, 2-1-2; lanes 3 and 10, 2-5-2; lanes 4 and 11, 2-7-1; lanes 5 and 12, 2-7-2; lane 6, C-3; lane 7, 2-7. The arrowheads indicate the positions of protected human IRF-1 probe.

(B) shows the detection of IRF-1 and -2 activities by gel shift analysis. Open and closed triangles indicate positions of the factor-DNA complexes of IRF-1 and IRF-2, respectively. The endogenous murine IRF-1 activity becomes detectable in lanes 3 and 6 only after prolonged exposure. Faster migrating bands probably represent the breakdown products of IRF-1 and/or IRF-2 bound to the DNA probe. Slower migrating bands in lanes 4, 5, 7, 8, 10 and 11 represent the DNA probe bound by two IRF-2 molecules.

(C) shows the results of Northern blot analysis of five micrograms of IRF-2 RNA using a mouse IRF-2 cDNA and a human 3-actin pseudogene, respectively as probe.

(D) shows the growth curves of the C-3, 2-7, 2-7-3 and 2-7-4 cell lines. Growth profiles are indicated for C-3 (open boxes), 2-7 (filled triangles), 2-7-3 (open triangles) and 2-7-4 (open circles).

Figure 9:
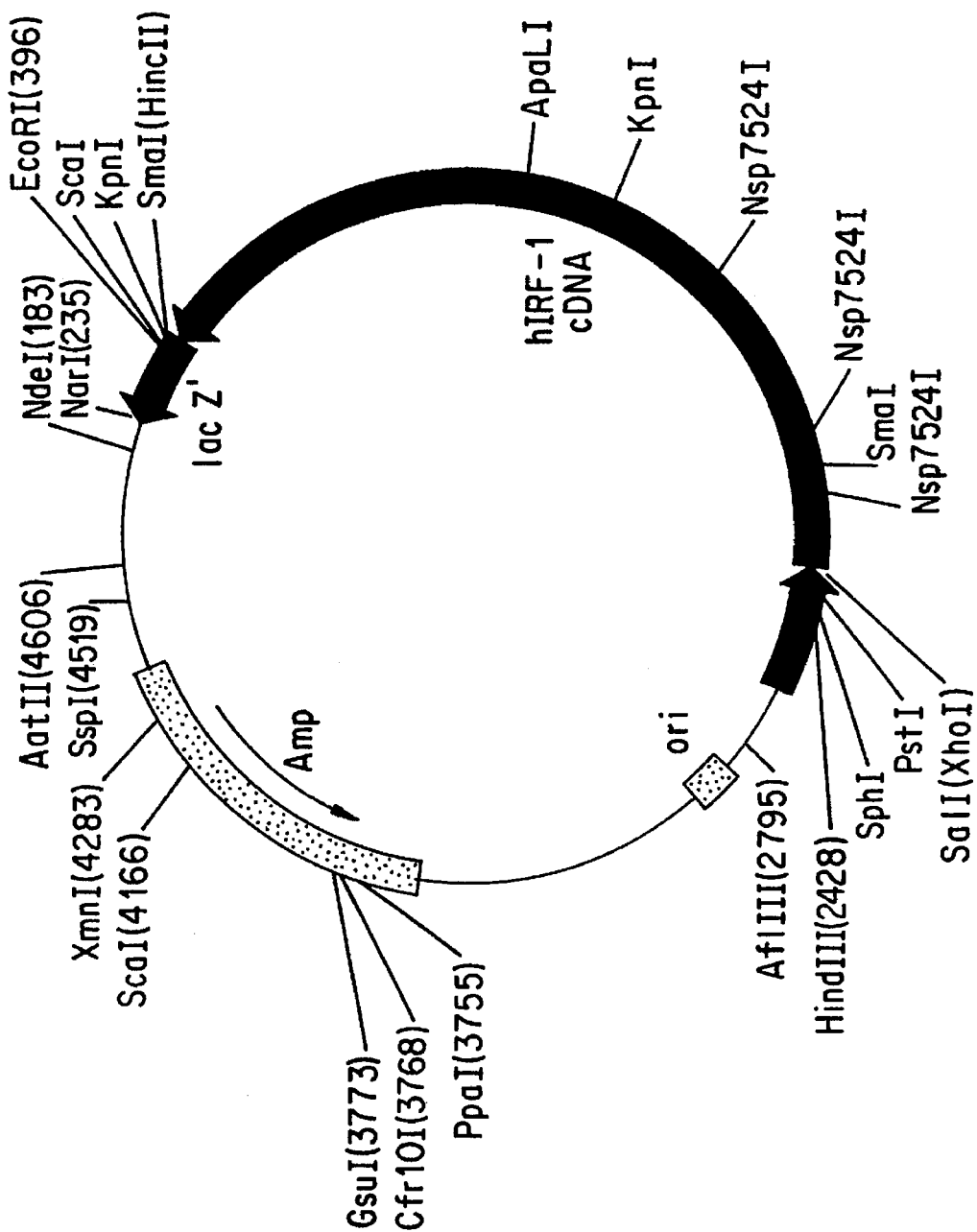

FIG. 9 depicts a restriction map of pUCIRF-1.

Figure 10:
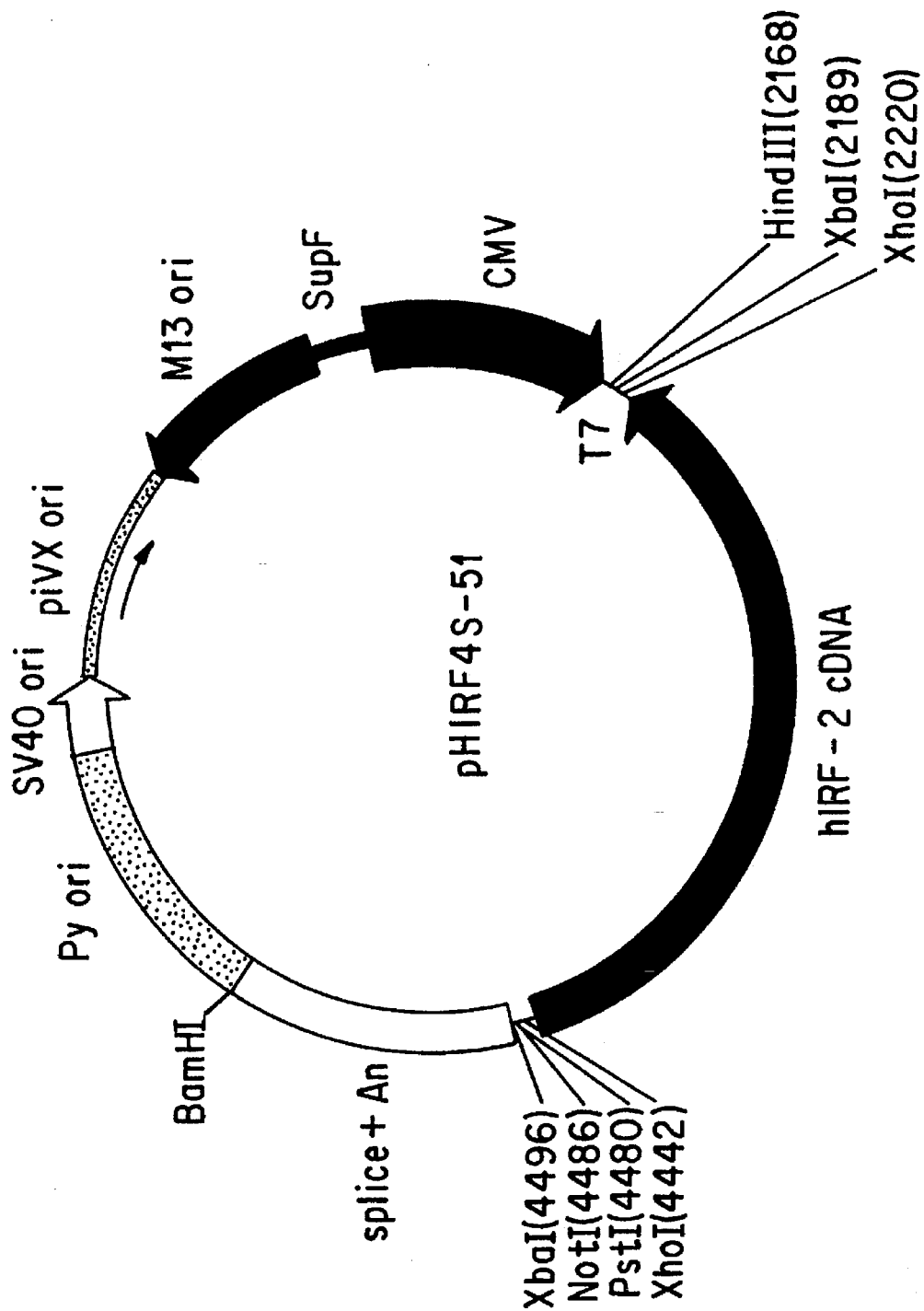

FIG. 10 depicts a restriction map of pHIRF4S-51.

DETAILED DESCRIPTION OF THE INVENTION

The present invention is predicated on the finding that IRF-1 is a tumor suppressor gene one or both of the alleles of which are deleted or mutated in various cancer patients, and that it maps to 5q31.1, the "critically deleted region" in del(5q); and that subtle changes in the ratio of IRF-1 to its structurally-related transcriptional repressor IRF-2 can have profound effects on cell growth whereby IRF-1 exhibits anti-oncogenic properties while, in contrast, overexpression of IRF-2 promotes tumorigenesis.

According to one aspect of the inventions there is provided a method of diagnosing tumorigenic mammalian cells or the propensity of a mammalian cell to become tumorigenic, which comprises:

a) selecting a parameter related to the capability of a said cell to produce IRF-1;

b) defining a value for the parameter which is taken to correspond to a capability of said cell to produce a tumor suppressing amount of IRF-1;

c) removing a sample of said cells from said mammal and subjecting said cells to an analysis to determine the value of said parameter for a cell in said sample;

d) comparing the determined value from c) with the defined value from b).

As described below the preferred parameters are the intracellular IRF-1/IRF-2 molar ratio, the presence or absence of one or more genes coding for IRF-1 on chromosome 5, or the presence of one or more mutations in one or more of the genes coding for IRF-1 on chromosome 5, or the presence or absence of chromosome 5.

Preferably the IRF-1/IRF-2 ratio is taken to correlate with the ratio of mRNA molecules per cell coding for IRF-1 and IRF-2 respectively. The values for mRNA molecules per cell can be determined e.g. by S1 nuclease mapping according to known methods (see, for example, Maniatis et al., Molecular Cloning, A Laboratory Manual, Cold Spring Harbor, N.Y., Cold Spring Harbor Laboratory (1982)), using as probes labelled DNAs corresponding to at least a fragment of the IRF-1 and IRF-2 genes respectively. Suitable probes preferably encompass the promoter regions of the genes, e.g. about −100 to +150 of the genes, preferably about −50 to about +100 (relative to the major cap site) and in the example described below −46 to +97 (relative to the major cap site at +1) of the human genes, in the case of working with human cells. Preferably analysis is carried out using probe DNA from genes of the same animal species as the cells under investigation. The mRNA molecule count can be carried out in known manner according to the particular label used. In the embodiment described below the probes are radiolabelled and the mRNA copy numbers of IRF-1 and IRF-2 can be obtained in known manner by densitometric analysis. Cells numbers would be determined in known manner.

Another preferred method involves immunometric immunoblot analysis of the intracellular IRF-1/IRF-2 protein content using labelled antibodies which specifically recognize IRF-1 and IRF-2 respectively. In one such method total cellular protein content is isolated, contacted with respectively labelled anti-IRF-1 and IRF-2 antibody, and the resulting intensity of the label determined: preferably this method will follow the procedure of a Western blot analysis followed by densitometric analysis of the resulting stain or label. Preferably the antibodies will be radiolabelled, or labelled with luciferase and densitometric analysis of the stains or labels will provide values for protein contents in known manner.

An additional or alternative approach for the detection of IRF-1/IRF-2 ratios and which is routinely used for the detection and quantitation of cell surface and intracellular proteins in intact normal or neoplastic hematopoietic cells (as well as cells from any lineage) is flow cytometric immunophenotyping (see the chapter of Willman, C. L., "Flow Cytometric Analysis of Hematologic Specimens", *Neoplastic Hematopathology*, Knowles, D. M., ed., Williams and Wilkens, Baltimore, Md. (1992)). Like Western blotting, this is also an immunologically-based technique but in contrast to Western analysis which is performed on isolated proteins, immunophenotyping would apply fluorescently-labelled antibodies (preferably monoclonal), directed towards the IRF-1 and IRF-2 proteins directly to intact permeabilized cells in suspension. The fluorescently-tagged cells would then be detected in a flow cytometer. By using two different fluorochromes (fluorescent dyes) conjugated to different antibodies for IRF-1 and IRF-2 (see pages 177 and 181-182 in this chapter of the above reference (Willman, C. L., ibid. (1992))for multicolor fluorescence analysis in flow cytometry), the IRF-1 and IRF-2 protein levels could be detected, measured, and correlated in each individual cell under analysis. This is an advantage to flow cytometric analysis, it provides information about individual cells and cell populations in the suspension under analysis, whereas Western analysis looks at total proteins isolated from all of the cells in the suspension. Other advantages of flow cytometry include its speed (analysis complete in less than 24 hours), the ability to correlate IRF-1/IRF-2 ratios with the expression of other cell surface proteins in hematopoietic cells, and the ability to distinguish neoplastic from non-neoplastic cells prior to analysis to allow the differential determination of IRF-1/IRF-2 ratios in neoplastic vs. residual normal cells in the suspension. A detailed methodological approach that could be used is provided in the Appendix 2 (to the above mentioned chapter) in which intracellular IgM proteins are quantitated in flow cytometry in hematopoietic cells to an appropriate analogous procedure anti-IRF-1 or anti-IRF-2 antibodies are substituted for the mouse antihuman IgM antibody in step 6.

When the chosen parameter is the number of alleles in chromosome 5 coding for IRF-1 the number of the alleles is determined preferably by carrying out a procedure for labelling such alleles using a labelled IRF-1 DNA probe. A preferred procedure is the known fluorescence in situ hybridization or FISH procedure.

Depending upon the diagnostic procedure and the patient, the approach will be variable.

To determine if an individual has a constitutional, germ-line deletion of IRF-1 that is predisposing to the development of cancer, it is suitable to quantitate the number of IRF-1 alleles in normal lymphocytes isolated from peripheral blood. Interphase nuclei can be examined; alternatively the cells can be induced into mitosis with a mitogen to obtain metaphase chromosomes from these cells. To examine IRF-1 deletions in interphase cells, it is preferable to use a genomic IRF-1 clone that is at least 8–10 kb in length; shorter probes do not give adequate hybridization signals in interphase nuclei. Longer clones are preferable and consistent hybridization signals have been achieved with an IRF-1 genomic clone of 19 kb. To examine IRF-1 deletions in metaphase chromosomes, shorter probes may be used. In this setting, the IRF-1 cDNA clone could also be used but the 19 kb IRF-1 genomic clone was found to be preferable.

To quantitate the number of IRF-1 alleles in a tissue biopsy or aspirate for a suspected cancer diagnosis, interphase FISH studies may be performed. Again, it is essential to use a genomic IRF-1 probe of at least 8–10 kb in length, as discussed above. If these cells were naturally in mitosis due to their pre-neoplastic or neoplastic state, then metaphase chromosomes could be examined from mitotic cells present in the aspirate or biopsy. Similar comments as discussed above apply to the use of suitable IRF-1 probes for metaphase analysis.

IRF-1 genomic or cDNA probes may be isolated in known manner from a suitable plasmid vector containing these DNA fragments.

DNA from the probe can then be labelled e.g. fluorescently in known manner, e.g. by nick translation.

The hybridization investigation is suitably performed on DNA extracted from the cell and denatured, in a manner similar to that described by Kuo et al., in *Am. J. Hum. Genet.*, 49: 112–19.

Suitable labels for the probe DNAs are dinitrophenol CDNP-11-dUTP or digoxagenin-11-dUTP the former of which can be developed with e.g. fluorescein isothiocyanate conjugated goat-anti rat-IgG and the latter of which can be developed using e.g. rhodamine-labelled antidigoxigenin antibody.

Cells are scored as having 2, 1 or 0 hybridized domains. Normal cells, which have a low propensity to become tumorigenic, have two alleles coding for IRF-1. By the fluorescence hybridization method it can be readily determined whether cells suspected of having a propensity for becoming tumorigenic have the optimal number of alleles or are deficient in one or both alleles.

The parameter may also be a structural rearrangement of allele or alleles coding for IRF-1. Such structural rearrangements lend themselves to detection using Southern blotting or slot blotting. In these procedures full-length IRF-1 cDNA isolated from a IRF-1 cDNA-containing plasmid such as pHIRF31 may be used as a suitable probe.

Suitable isolated genomic probes from samples of the cell under investigation can be digested by various nucleases chosen from e.g. BglII, BamHI, EcoRI, HindIII, KpnI, PstI and XbaI. After blotting on a suitable filter the digest can be hybridized with the cDNA probes labelled e.g. by the random primer method.

The analysis may be carried out first on corresponding cells from corresponding mammals considered to have a low or nil propensity to become tumorigenic to provide a defined value standard corresponding to the IRF-1 content of such cells which does not suffer from rearrangement and can thus produce a tumor suppressing amount of IRF-1.

Quantitative DNA analysis by slot blotting can be carried out in a similar manner using genomic DNA from the cell under investigation and controls. After suitable denaturing the blots are hybridized to labelled IRF-1 cDNA probe e.g. as described above and quantitated by suitable methods e.g. laser-scanning densitometry.

Preferably in the Southern and slot blotting each blot is subsequently stripped and rehybridized with a DNA probe which maps to a location on chromosome 5 different from that containing IRF-1 alleles e.g. 5q22 or preferably 5p, a suitable DNA probe is a cDNA probe for complement component 9. Such a probe will act as a control probe to provide an internal standard against which to quantitate IRF-1 deletions. The IRF-1 and corresponding C9 autoradiographic signals can be quantitated and the IRF-1; control (e.g. C9) hybridization rate determined for each sample.

As described below the above mentioned Southern and slot blotting may be used also to detect the presence or absence of IRF-1 alleles which do not suffer from rearrangement, by virtue of a decrease in the IRF-1 hybridization signal compared with controls indicating loss of one or both alleles and thus increased propensity of the cell to becoming tumorigenic.

When the chosen parameter is mutation of one or both IRF-1 alleles, such mutations may be determined by sequencing appropriate fragments of the genomic IRF-1 DNA under investigation and comparing this with corresponding fragments from controls or published IRF-1 DNA sequences. The analysis is preferably carried out on genomic DNA. The resulting digest DNA after suitable work-up can be multiplied by PCR using suitable primers and orientations: after size separation using e.g. agarose gel electrophoresis the desired DNA fragments can be cloned into a suitable vector e.g. pBluescript and after multiplication the insert can be removed by suitable digestion and sequenced in known manner. Point and more extensive mutations in the sequenced DNA may indicate a loss of function of one or more IRF-1 alleles in a tissue sample.

The HindIII approach used for sample 10, described below, was designed specifically for the cloning of the rearranged fragment in this patient. Depending upon the setting screening could be carried out for individuals who carry an IRF-1 deletion or mutation in the germline and thereby they and all of their progeny would be at risk for subsequent cancer development (analogous to the situation from the p53 tumor suppressor gene; see Malkin et al., Science 250: 1233–1238 (1990)). In this setting specific IRF-1 exons for DNA isolated from peripheral blood lymphocytes would be amplified, individual exons would be primed and amplified using PCR, and these amplified products screened for mutations by the techniques described below. Alternatively, tissue samples or aspirates from potentially neoplastic lesions could be screened for IRF-1 mutations that were either present in the germline or somatically acquired. In this setting, to detect deletions or mutations in the tumor, DNA isolated from cells present in the aspirate or biopsy would be used. Again, primers to the different IRF-1 exons would be used to prime the specific exons from total DNA and these exons would be screened for mutations e.g. by one of the following procedures:

1. RNAse protection using methods of Kinzler et al., Science 253: 661–664 (1991);
2. cloning the amplified PCR fragments and sequencing of the cloned fragment, or alternatively, directly sequencing the PCR-amplified product without cloning;
3. SSCP: PCR fragments are screened for mutations by single strand conformation polymorphism analysis. This screening procedure has been particularly useful for detecting mutations in the analogous p53 gene (see Mashiyama et al., Oncogene 6: 1313–1318 (1991) and the original reference Orita et al., PNAS USA 86: 2766–2770 (1989)).

A further aspect of the invention provides a cloned DNA for reducing the propensity of a mammalian cell to become tumorigenic or suppressing the tumorigenic phenotype of such a cell which includes a DNA sequence coding for IRF-1. Preferably such a cloned DNA includes a DNA sequence coding for human IRF-1.

The above cloned DNAs are suitable for use in a method of reducing the propensity of a cell to become tumorigenic or suppressing the tumorigenic phenotype of such a cell by using the cloned DNA coding for IRF-1 and delivering the cloned IRF-1 DNA to the cell. Alternatively the method of reducing the propensity of a cell to become tumorigenic or of suppressing the tumorigenic phenotype of a cell may comprise delivering IRF-1 to the cell.

Methods for the delivery of DNA into a cell to change the phenotype or effect treatment of disease are described in numerous publications, which are conveniently reviewed in Miller, Nature 357: 455–460 (11 Jun. 1992). The methods described in the literature include, e.g. direct injection of liposome/plasmid DNA complexes into tumor masses and the use of retrovirus vectors and adenovirus vectors. A method involving the targeting of the DNA to the transferrin receptor by complexing the DNA with transferrin has been shown to be improved by the concomitant use of adenovirus (see, e.g. Cotten et al., Proc. Natl. Acad. Sci. USA 89: 6094–6098 (1992); Wagner et at., Proc. Natl. Acad. Sci. USA 89: 6099–6103 (1992); Curiel et at., Proc. Natl. Acad. Sci. USA 88: 8850–8854 (1991)).

The introduction of a wild-type copy of the retinoblastoma gene (RB) into retinoblastoma cells suppressed their tumorigenic properties in nude mice (see PCT Intl. Appl. 9005180, published 17 May 1990, which describes a strategy for replacing inactive or defective RB genes by constructing a retrovirus containing RB cDNA and using it to infect a retinoblastoma cell line).

European Patent Application publication No. 0475623, published 18 Mar. 1992, describes a strategy for replacing inactive or defective p53 genes using recombinant retroviruses derived from Moloney murine leukemia virus to introduce wild-type p53 under LTR promoter control into e.g. Osteosarcoma cell line Saos-2.

Examples of other publications detailing suitable strategies for carrying out gene therapy include Roemer et al., Eur. J. Biochem. (FEBS) 208: 211–225 (1992), which describes inter alia the construction of viral vectors; European Patent Application Publication No. 386766 which describes the introduction of DNA into cells by microinjection to modify a gene within the genome of intact mammalian cells; PCT Patent Application WO 9200329 which describes the transfecting of tumor infiltrating lymphocytes of a patient with the DNA of p53 and reintroducing the cells into the patient;

PCT Patent Application WO 9107487 which describes the transfer of a gene coding for somatotropin into vertebrate cells or tissue using microprojectiles; and PCT Application WO 9207573 which describes the insertion of genetic sequences into endothelial cells using infective recombinant retrovirus.

The insertion of the IRF-1 gene into selected cells either directly into the mammal or by transfecting or infecting cells removed from the mammal followed by reintroducing infected cells into the mammal can be carried out analogously to the procedures described in the above publications.

The present invention also permits a therapeutic strategy whereby cells, preferably hematopoietic stem cells containing IRF-1 deletions or mutations can be selectively eliminated ex vivo from the total population of stem cells, and the normal stem cells thereafter selectively expanded at the expense of the stem cells with the IRF-1 deletions or mutations, followed by the autologous transplantation of corrected marrow or peripheral blood cells to the patient. Such a method of treatment would comprise removing tissue from a patient, screening the tissue for cells having no IRF-1 deletions or mutations expanding the population of such cells and reintroducing them to the patient by e.g. infusion or autologous transplantation.

Yet a further aspect of the present invention comprises a kit for detecting the sequence of the IRF-1 gene or mutation thereof by the polymerase chain reaction, which comprises a carrier means having in close confinement therein one or more container means such as vials, tubes, and the like. For example, a first container means may contain a set of pairs of single standard DNA primers, the set allowing synthesis of all of the IRF-1 coding sequence or a fragment thereof. A suitable pair of single stranded DNA primers are described below. The use of such a kit may follow generally the procedure using PCR described below in the examples. The kit may also contain other container means which are used to carry out the PCR reaction, e.g. a DNA polymerase, buffers; etc.

Still a further aspect of the invention comprises a kit for determining the IRF-1/IRF-2 ratio of a cell or tissue which comprises in separate container means anti-IRF-1 antibody and anti-IRF-2 antibody, said antibodies having no or substantially no cross reactivity with the other antigen and being preferably monoclonal. The antibodies may be labelled or can be labelled at the time of use. The label will be such as to enable determination of the amounts of the antigen in the cell upon appropriate analysis.

Such a kit may be suitable for use e.g. in immunoblot analysis on isolated proteins or immunophenotyping/flow cytometric analysis for analysis of protein levels in individual cells and correlation with other cell surface or cytoplasmic proteins (phenotypic markers), or with DNA content and S phase fraction.

The antibodies can be prepared in known manner, e.g. by fusing spleen cells from an animal immunized with IRF-1 or IRF-2, or selected epitopes thereof, with myeloma cells and subsequently isolating a hybridoma clone which produces an respective anti-IRF antibody. Such antibodies may for example neutralize the IRF-1 or IRF-2 activity respectively, but would not be cross reactive. Suitable procedures for the preparation of such antibodies and the selection of potential antigenic epitopes thereof are disclosed in New Zealand Patent No. 222006, European Patent Application No. 90106568.0 (corresponding to U.S. patent application No. 801048, filed Dec. 3, 1991) and Hopp et al., *Mol. Immunol.* 20(4): 483–489 (1983)), and PCT Application WO 8003564.

Still a further aspect of this invention comprises a kit for determining the number of IRF-1 alleles in a mammalian tissue sample using fluorescent in situ chromosomal hybridization which comprises a fluorescently labelled DNA sequence or DNA which is capable of being fluorescently labelled which is capable of hybridizing to the IRF-1 genome in metaphase chromosome or interphase nuclei. The DNA sequence may be e.g. a cDNA clone (for use in hybridizing to metaphase chromosomes) or a genomic clone of at least about 8–10 kb length (for hybridizing to intact interphase nuclei). The number of alleles may be counted using fluorescence microscopy. Further internal controls for this procedure include single copy DNA probes derived from the same chromosome as IRF-1 and IRF-2 but located a suitable distance away from the regions of interest (e.g. 5q31 for IRF-1 and 4q for IRF-2). By this means allele numbers can be determined in tissue samples, inappropriate allele numbers thereby predisposing to malignancy.

The present invention is described in further detail in the following non-limiting Examples.

EXAMPLE 1

The presence and precise location of the IRF-1 gene on human chromosome 5q was determined using fluorescence in situ hybridization (FISH) techniques to map an IRF-1 probe on normal metaphase chromosomes generated from PHA-stimulated lymphocytes. A 19 kb IRF-1 genomic clone containing the IRF-1 promoter and all 10 coding exons (Yamada et al., ibid. (1991); see FIG. 4A) was fluorescently-labelled and hybridized to fixed metaphases (see Pinkel et al. *Proc. Natl. Acad. Sci. USA* 85: 9138–9142 (1988), Sakamoto et al., *II System Performance* (1992)) as described below.

Probes detecting sequences localized in 5q22 and 5q31 (IRF-1) were modified differentially to allow dual color visualization of hybridized domains in interphase and metaphase. A 19 kb DNA probe (Cyn 5.120) localizing to 5q22, provided by R. White (University of Utah, Salt Lake City, Utah), was modified by nick translation (Pinkel et al., ibid. (1988)) with dinitrophenol (DNP)-11-dUTP (Novagen, Madison, Wis.). The IRF-1 genomic DNA probe (19 kb; Yamada et al., ibid. (1991)) was chemically modified with digoxigenin-11-dUTP (Boehringer Mannheim, Indianapolis, Ind.). Probes were recovered at a concentration of approximately 20 ng/µl by using Sephadex G-50 spin columns. All labelling reactions were adjusted to produce labelled probes whose individual elements were 0.3–1.0 kb in length.

Single and dual color hybridizations were performed using a modification of the procedures described by Kuo et al., ibid. (1991). Target DNA in Carnoy's fixed cells on slides was denatured by immersion in 70% formamide and 2X SSC for 3 min at 73° C. The slide was then dehydrated by submersion in successive ethanol solutions (70%, 85% and 100%). After dehydration the slides were treated with proteinase K (2.5 µg/ml) or 3 min at 38° C.

Occasionally aged samples showed low hybridization efficiency and were digested for longer periods of time (4–8 min). Following digestion, slides were dehydrated as previously described. The hybridization mixture (10 µl total volume consisting of 50% formamide, 2X SSC, 10% dextran sulfate, 1–5 µg human placental DNA and 20 ng of each probe) was denatured at 73° C. for 5 min and incubated at 38° C. for 20 min. The mixture was applied to slides containing cells and sealed under a coverslip. The slides were incubated for approximately 12 hours at 37° C. After hybridization the slides were washed for 10 min in three changes of 50% formamide at 48° C. followed by successive washes in 2X SSC and 0.2X SSC at the same temperature. The hybridized regions were treated with 50 μl of 4X SSC, 1% BSA for 5 min. The slides were then treated with 4 X SSC mixture containing rat-anti-DNP (0.5 μl/ml; Boehringer Mannheim) and rhodamine-labelled anti-digoxigenin (Novagen) for 30 min at room temperature followed by four, 10 minute washes at room temperature; 4X SSC, 4X SSC+ 0.1% triton X-100, 4X SSC, and PN buffer (0.1M dibasic sodium phosphate, 0.1M monobasic sodium phosphate, 0.05 NP-40, pH 8). Following treatment with PNM (PN buffer, 5% nonfat dry milk and 0.02% sodium azide; centrifuged to remove solids), fluorescein isothiocyanate conjugated goat-anti-rat IgG (16.6 μg/ml; CalTag, Burlingame, Calif.) was applied for 30 min and cells washed 4 times in PN buffer for 10 minutes. Prior to microscopic analysis, cells were stained with 4,6-diamidino-2-phenylindole (DAPI) in antifade solution (Johnson and de C. Nogueira Araujo, *J. Immunol. Methods* 43: 349–350 (1981)).

Fluorescence microscopy with appropriate filters was accomplished as described by Pinkel et al., *Proc. Natl. Acad. Sci. USA* 83: 2934–2938 (1986), ibid. (1988). In single color hybridization using the IRF-probe alone, all cells in the microscope field were scored as having 2, 1 or 0 domains. In dual color hybridization, IRF-1 domains were scored in cells showing at least one green-FITC-linked 5q22 hybridization domain.

Preparations in which >25% of the cells did not contain a hybridization domain or in which <50 cells could be analyzed and scored were excluded from data analysis.

Figure 1B:
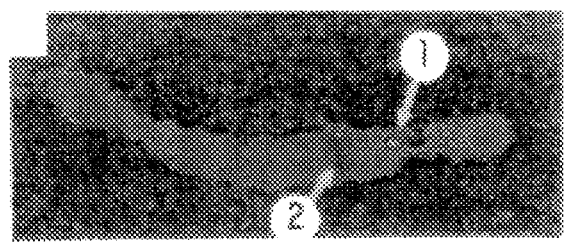
In FIG. 1B, which shows a computer assisted microanalysis of chromosome 5 from a normal metaphase hybridized with an IRF-1 probe (arrow 1) and a unique genomic probe complementary sequences at 5q22 (arrow 2), the IRF-1 gene was mapped to 5q31.1 relative to the short arm telomere.

The IRF-1 probe hybridized only to sequences on chromosome 5q, as shown in FIG. 1A. IRF-1 was precisely mapped to chromosome 5q31 with computer-assisted fluorescence microscopic analysis of the hybridized metaphases (Sakamoto et al., ibid. (1992)). As indicated in FIG. 1B, this computerized mapping method automatically acquired multi-color images of total chromosomal DNA, the fluorescently-labelled IRF-1 probe, and a fluorescently-labelled probe hybridizing to 5q22 used as a control (discussed in detail below). The IRF-1 gene was mapped to 5q31.1 by analyzing 15 hybridized metaphases and is reported as a fractional location relative to the short arm telomere of chromosome 5.

EXAMPLE 2

To determine whether IRF-1 was deleted or structurally rearranged in hematopoietic neoplasms with interstitial deletions or translocations involving chromosome 5q31, cryopreserved cell suspensions were selected from 11 representative cases of acute leukemia and MDS with del(5q) and two cases of de novo AML with reciprocal translocations of 5q31 that had sufficient cells for analysis. These samples included: 4 cases of preleukemic myelodysplasia (MDS), including 2 classic cases of the 5q-Syndrome with Refractory Anemia (Samples 1–4); two cases of Refractory Anemia with excess Blasts (RAEB) that had transformed to AML (so-called "secondary AML") (Samples 5, 6); 5 cases of de novo AML (Samples 7–9, 12, 13), one case of de novo ALL (Sample 10), and one case of AML in relapse following initial treatment with combination chemotherapy (Sample 11). The complete karyotype and, where appropriate, the leukemia blast cell percentage in the cryopreserved sample under analysis are included for each sample in Table 1 (Columns 3 and 4). Similarly cryopreserved cell suspensions from normal human bone marrow and peripheral blood were used as controls (Samples 16, 17). Two hematopoietic neoplasms with translocations of chromosome 5q involving regions other than 5q31 were also selected as controls (Samples 14, 15); a case of MDS of the Chronic Myelomonocytic Leukemia (CMMoL) subtype with a reciprocal translocation involving 5q33 and a case of Ki-1+Non-Hodgkin's Lymphoma with t(2;5)(q23;q35).

IRF-1 deletions and structural rearrangements were assessed in Southern blots and quantitative slot-blots using a full-length IRF-1 cDNA (pHIRF31) as a probe (Maruyama et al., *Nucl. Adds Res.* 17: 3292 (1989)). To provide an internal standard against which to quantitate IRF-1 deletions, each blot was subsequently stripped and rehybridized with a cDNA probe for complement component 9 (C9;pHLC9.55) (DiScipio et al., *Proc. Natl. Acad. Sci. USA* 81: 7298–7302 (1984)) which maps to 5q13 (Abbott et al., *Genomics* 4: 606–609 (1989)). These procedures were carried out as follows:

High molecular weight DNA was isolated from the thawed leukemic, MDS, and control samples, previously cryopreserved a cell suspensions in fetal calf serum (90%; Hyclone) and DMSO (10%; Sigma) at −135° C. Leukemic blasts and myeloid precursor cells were enriched at the time of initial sample receipt by centrifugation over Ficoll-Hypaque (Sigma); the mononuclear cells were isolated, blast cell counts were determined by morphologic review, and samples were cryopreserved as described. For Southern blot analysis, the genomic DNA from the patient samples and controls was digested with BglII, BamHI, EcoRI, HindIII, KpnI, PstI, or XbaI. Five micrograms of DNA per sample was electrophoresed in 0.8% agarose gels, blotted onto nitrocellulose or Hybond-N+ (Amersham), and hybridized with cDNA probes labelled by the random primer method (Sambrook et al., *Molecular Cloning, A Laboratory Manual,* Cold Spring Harbor, N.Y., Cold Spring Harbor Laboratory (1989)). Each blot was washed under high stringency conditions.

For quantitative DNA analysis, genomic DNA from the patient samples and control's was subjected to alkaline denaturation followed by neutralization and was subsequently blotted onto nitrocellulose at three different dilutions of 2 μg, 1 μg and 0.5 μg (Sambrook et al., ibid. (1989)). Conditions for hybridization were identical to those used for Southern blots. Both Southern and slot blots were first hybridized to the IRF-1 cDNA probe excised from plasmid pHIRF3: (Maruyama et al., ibid. (1989)) detecting a 6.0 kb HindIII fragment, then stripped and rehybridized to the complement C9 cDNA control probe excised from plasmid pHLC9.55 (DiScipio et at., ibid. (1984)) detecting a 3.0 kb band.

The IRF-1 and corresponding C9 autoradiographic signals were quantitated with laser-scanning densitometry of matched autoradiographics using computer assisted FOTO/ANALYST imaging analysis system (Fotodyne, N.Y.), and the IRF-1:C9 hybridization rate was determined for each sample.

Figure 2:
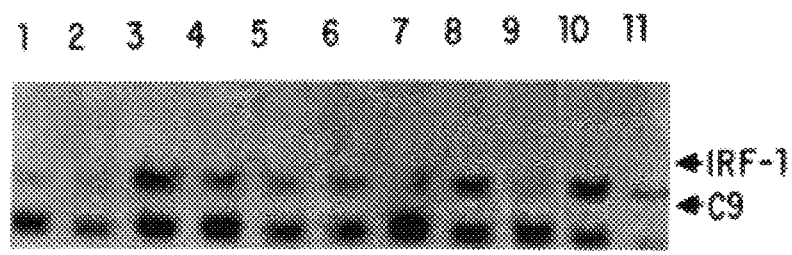
In FIG. 2 which is a Southern blot of HindIII-digested DNA from normal controls and from leukemia and MDS samples (see also Table 1), the filter was initially hybridized with an IRF-1 cDNA probe detecting a 6.0 kb fragment, then stripped and rehybridized with the C9 probe detecting a 3.0 kb bond as an internal control. The Lanes correspond to the following samples (as designated in Table 1): 1(9), 2(1), 3(13), 4(3), 5(5), 6(6), 7(8), 8(10), 9(7), 10 (normal bone marrow control; 5 µg), 11 (normal bone marrow control; 2.5 µg).

The results are shown in Table 1 and FIG. 2.

In FIG. 2 each Lane corresponds to the following samples (as designated in Table 1): 1(9), 2(1), 3(13), 4(3), 5(5), 6(6), 7(8), 8(10), 9(7), 10 (normal bone marrow control; 5 μg), 11 (normal bone marrow control; 2.5 μg).

As shown in FIG. 2, a significant reduction in IRF-1 hybridization signals was observed in each case of MDS and de novo AML with del(5q) (Table 1, Samples 1–11) and is indicated by a decrease in the IRF-1:C9 hybridization ratio as compared to controls (Table 1, Samples 14–17). Decreases in the IRF-1:C9 hybridization ratio corresponded closely with the percentage of leukemic blasts in each sample and with the cytogenetic frequency of cells with a del(5q) (Table 1). In addition to a significant decrease in the IRF-1 hybridization signal, structural rearrangements of the IRF-1 gene were also observed in Sample 10 and were characterized in detail as described below.

Interestingly, a significant decrease in the IRF-1 hybridization signal was also detected in each case of de novo AML with a reciprocal translocation involving chromosome 5q31 (Table 1, Samples 12, 13; FIG. 2); decreases in the IRF-1:C9 hybridization ratio again corresponded to the percentage of leukemic blasts in each case. No rearrangements of the IRF-1 coding exons were detected in Southern blots and no rearrangements were seen within 197 kb of the IRF-1 gene using pulsed-field gel electrophoresis in these samples. In contrast, both IRF-1 alleles were retained in the control case of CMMoL with a reciprocal translocation of 5q33 and the lymphoma sample with a reciprocal translocation involving 5q35 (Table 1, Samples 14, 15).

The fact that IRF-1 was deleted in each of the 13 cases of MDS and leukemia with del(5q) or translocation 5q31 is highly significant since these samples were representative of the entire spectrum of hematopoietic neoplasms that have been reported to present with del(5q) (see Nimer and Gold, ibid. (1987)). Furthermore, IRF-1 deletions were recently detected in an additional four cases of MDS and acute leukemia with del(5q).

EXAMPLE 3

Deletion of IRF-1 in Human Leukemia and Myelodysplasia: Analysis by Single and Dual Color Interphase Cytogenetic Analysis Interphase cytogenetic investigations were carried out as described above in Example 1 (Pinkel et al., ibid. (1986), ibid. (1988)). The single and dual color fluorescence in situ chromosomal hybridization (FISH) studies were performed on the same cryopreserved samples that were used for determination of IRF-1:C9 hybridization ratios. For single color FISH studies, the 19 kb IRF-1 genomic DNA (Yamada et al., ibid. (1991)) was chemically modified and hybridized to slides containing fixed cell suspensions (Table 1, Samples 1–10, 12, 13, 15–17) or to slides prepared from residual fixed cells remaining after cytogenetic analysis (Table 1, Samples 11, 14). All cells in the microscopic field were scored as having 2, 1, or 0 IRF-1 hybridization domains (alleles); 1000 total cells were scored in the majority of samples (Table I, Column 6). In the control samples that lacked IRF-1 deletions (Table 1, Column 7, Sample 14–17) IRF-1 alleles were detected in 84–90% of cells. However, on average, 10% of these control cells had only 1 and 2.4% of cells had no detectable IRF-1 hybridization domain. This slight decrease in FISH hybridization efficiency in the cryopreserved controls, relative to fresh lymphocytes which have 2 IRF-1 alleles detectable in 92–95% of cells and 1 or no IRF-1 hybridization domain in 5–8% of cells, results from the use of cryopreserved samples stored 2–5 years and the use of a relatively short (19 kb) single copy genomic probe rather than a repetitive sequence probe for FISH studies (Pinkel et al., ibid. (1986), ibid. (1988)). However, compared to this established background, only 1 IRF-1 allele was detected in a significant percentage of cells in each MDS and leukemia sample with del(5q), varying from 24–88% of total cells (Table 1, Column 7, Samples 1–11). The loss of a single IRF-1 allele was also confirmed in the two de novo AML cases with reciprocal translocations of chromosome 5q31 (Table 1, Samples 12, 13). The IRF-1 single allele frequency obtained in these FISH studies correlated well with the leukemic blast cell percentage determined by morphologic criteria, when 1000 or more cells could be scored. Relative to the controls, several of the acute leukemia samples (Table 1, Column 7, Samples 7, 8, 10, 12, 13) also appeared to have a significant fraction of cells ($\geq 10\%$) with no IRF-1 hybridization domain, suggesting that both IRF-1 alleles might have been deleted in a subpopulation of leukemic cells.

Figure 3A:
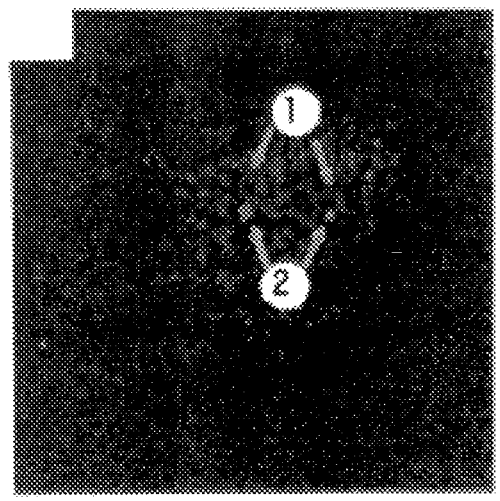
Figure 3B:
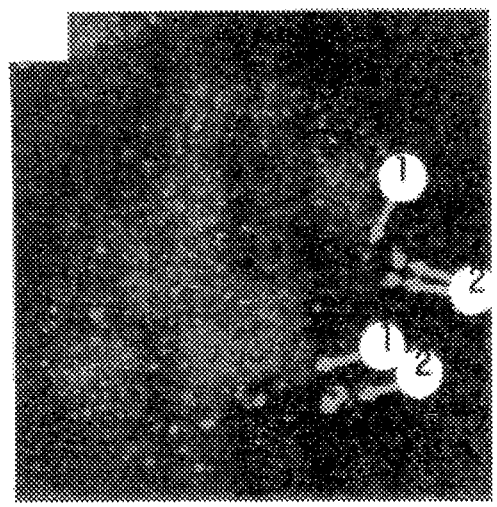
Figure 3C:
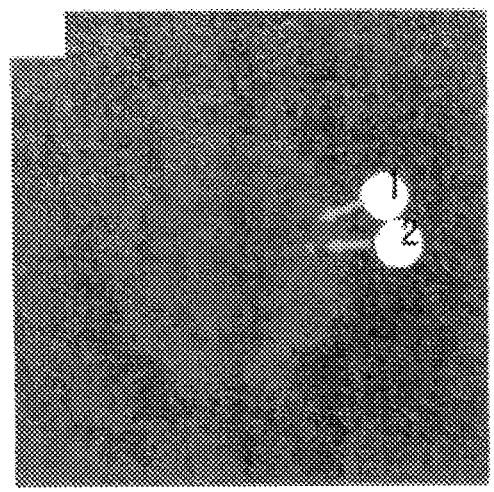

To perform more detailed studies of IRF-1 deletions, dual color FISH studies were performed on samples in which residual fixed cells were available. The 19 kb IRF-1 genomic probe and a 19 kb single copy genomic probe hybridizing to unique sequences at 5q22 (Cyn 5.120; see FIG. 1B) were differentially labelled to allow dual color visualization of hybridized domains in interphase as described by Pinkel et al., ibid. (1986), ibid. (1988)). Examples from representative samples are shown in FIG. 3. IRF-1 domains were scored only in those cells that contained at least one FITC-5q22 hybridization domain. Preparations in which less than 50 total cells could be analyzed and scored and in which greater than 25% of cells lacked any 5q22 hybridization signal were excluded from analysis (see Table 1).

In the dual color FISH assays performed on two of the control samples (Table 1, Column 9, Samples 15, 17), the frequency and distribution of IRF-1 and 5q22 alleles were quite similar; greater than 80% of cells contained the expected 2 IRF-1 and 2 5q22 hybridization domains. In these controls, cells containing various combinations of 1 or 2 IRF-1 and 5q22 domains comprised between 2.2–7.9% of all cells analyzed, and, only 2.0–4.3% of cells contained 2 5q22 domains and no detectable IRF-1 domain.

Blast populations definitively lacking both IRF-1 hybridization domains, but retaining 1 or 2 5q22 hybridization domains were identified in one of the 6 samples with del(5q) or translocation 5q31 analyzed by dual color FISH (Table 1, Column, 9, Sample 6). Both IRF-1 alleles were also deleted in 4/16 residual cells that could be analyzed in Sample 10, but this sample did not meet the inclusion criteria for FISH data since only 16 total cells could be analyzed (see Table 1). Both of the samples with a subpopulation of blasts that had both IRF-1 domains (alleles) deleted were from patients with acute leukemia; a case of RAEB in transformation to AML (Sample 6, 22% of cells with 0 IRF-1 domains) and the case of ALL just described (Sample 10; 25% of cells). In contrast, all samples of preleukemic MDS had a deletion of only one IRF-1 allele. Deletion of a single IRF-1 allele was also again confirmed in both of the de novo AML patients with a reciprocal translocation of 5q31 (Table 1, Column 9, Sample 12). Single color FISH analysis had suggested that Samples 7, 12, and 13 might contain a subpopulation of leukemic cells with deletion of both IRF-1 alleles (Table 1). This possibility was not directly confirmed by the dual color analysis; we observed a few cells that contained 5q22 while lacking IRF-1. However, it is possible that large deletions (see below and Table 1) could have removed both the 5q22 internal control and the IRF-1 gene in a subpopulation of cells in Samples 7, 12 and 13, since these cells would not have been scored in the dual color analysis. This latter possibility is in fact suggested by the relatively high frequency of cells that had already deleted one allele each of the 5q22 region and IRF-1 gene (Sample 7, 80.3%, Sample 12, 52.9%; Sample 13, 55.9%).

Dual color FISH analysis also revealed an unexpected heterogeneity in the location of the proximal breakpoint in three of the six cases with a del(5q). At the traditional cytogenetic level of resolution, samples 2, 6 and 7 were reported to contain a del(5)(q13q33); with these breakpoints, the clonal population would be expected to have 1 IRF-1 and 15q22 domain since the remaining IRF-1 and 5q22 domains should both have been deleted from chromosome 5q. However, in addition to a population containing 1 IRF-1/1 5q22 allele, a significant population of cells was also identified that contained 2 5q22 and 1 IRF-1 domains in each sample (Table 1, Column 9, Samples 2, 6). These findings suggest that distinct blast populations with different proximal breakpoints (retaining or also deleting the 5q22 region) but with uniform deletion of an IRF-1 allele were present in these patient samples. Breakpoint heterogeneity was also observed in both of the de novo AML cases with translocation 5q31 (Table 1, Column 9, Samples 12, 13). If one IRF-1 allele was deleted during the translocation event (as demonstrated in the FISH assays), then the expected dual color allele frequency would be 2 5q22/1 IRF-1 in the majority of cells. However, in addition to this population, both AML cases had a significant fraction of cells with 1 5q22 and 1 IRF-1 allele (Table 1, Column 9). Since neither of the AML cases had a monosomy 5 in addition to the translocation 5q31, these results indicate that far more DNA was deleted from the translocation breakpoint region on chromosome 5 than has previously been detected at the cytogenetic level of resolution.

EXAMPLE 4

Screening Leukemia and Myelodysplasia Cases for IRF-1 Mutations

To determine if the retained IRF-1 allele in the remaining cases had sustained any smaller deletions/insertions or point mutations not detectable in the above analysis, the polymerase chain reaction (PCR) was used to prime the residual IRF-1 exon from DNA isolated from all leukemia and MDS samples with the exception of sample 5 and the PCR products were then screened for mutations by RNase protection analysis according to Kinzler et al., Science 251: 1366–1370 (1991) as described below.

A single base change was noted in exon 7 in four samples (Table 1, Samples 4, 6, 8, 10), this base change occurred within the third degenerate nucleotide in a codon but may not be of significance.

EXAMPLE 5

Characterization of a Breakpoint within the IRF-1 Gene

Figure 4B:
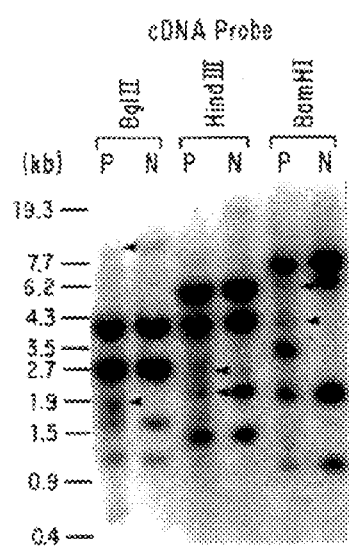

Southern blot analysis revealed structural rearrangements of the IRF-1 gene in Sample 10 (Table 1), a case of de novo ALL. In initial studies with the full length-IRF-1 cDNA probe (FIG. 4B, left panel), a deletion of several IRF-1 restriction fragments and the appearance of novel rearranged bands was observed. In the BglII-digested DNA, there was a deletion of the 13 kb fragment (containing IRF-1 exon; which arises from digestion of an upstream BglII site in genomic DNA and the BglII site in intron I; see FIG. 4A) and the appearance of a novel 1.8 kb fragment. Similarly, with HindIII, there was a reduction in the intensity of the 2.0 kb fragment (containing exons 1 and 2; FIG. 4A) and the appearance of a novel band at 2.4 kb. The 5.0 kb BamHI fragment (containing exons 1–3; FIG. 4A) virtually disappeared and a novel fragment was detected at 3.9 kb. The additional 2.8 kb BamHI fragment in the patient sample (FIG. 4B) resulted from a naturally occurring BamHI polymorphism; see FIG. 4A), for which the patient was heterozygous. These data are all consistent with the presence of a deletion involving the 5' end of the IRF-1 gene in the majority of cells in the sample. The detection of several novel bands using the IRF-1 cDNA probe indicates that there may also be another more complex IRF-1 rearrangement in a subpopulation of leukemic cells in this sample.

Figure 4C:
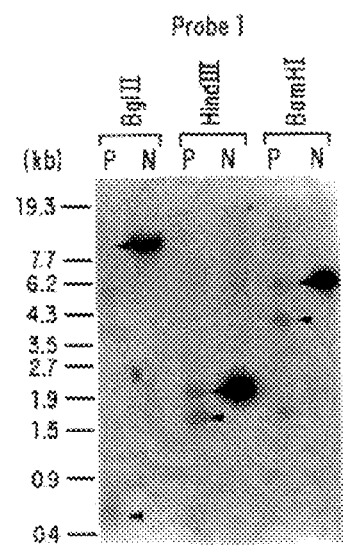
Figure 4D:
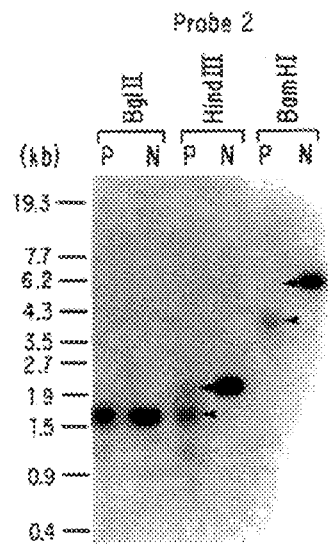

To more precisely determine the location of the major IRF-1 breakpoint in sample 10, additional Southern blots using subclones derived from the genomic IRF-1 clone as diagrammed in FIG. 4A were carried out; probe 1 was the HindIII-BglII fragment containing exon 1 and probe 2 was the BglII-HindIII fragment containing exon 2. Hybridization with probe 1 revealed IRF-1 structural rearrangement with each enzyme (FIG. 4C). In the BglII-digested DNA in the patient sample, the virtual disappearance of the 13 kb band and the appearance of a novel 0.5 kb band was again observed. With HindIII, the 2.0 kb band was remarkably reduced in intensity and a novel 1.4 kb band was evident while with BamHI, the 5.0 kb band was markedly reduced in intensity and a novel 3.9 kb band was detected. Using probe 2 (FIG. 4D), no deletions or rearrangements were evident in the BglII digest, implying that the breakpoint must lie 5' to the BglII restriction site in intron 1. Similar deletions and rearrangements were observed with probe 2 as were seen with probe 1 on HindIII- and BamHI-digested DNA (FIG. 4D).

These studies indicate that the predominant breakpoint in the IRF-1 gene in patient sample 10 (Table 1) lies approximately 400 bp 5' of the BglII site in intron 1 (FIG. 4A). To gain further insight into the nature of this rearrangement, a modification of the polymerase chain reaction inverse PCR; see Silver in PCR; A Practical Approach, McPherson et al., eds., Oxford IRL Press, pp. 137–146 (1991) was used to amplify and sequence the IRF-1 gene in the region encompassing exon 1 and intron 1 in both normal and leukemic DNA (FIG. 5).

Genomic DNA from the samples and normal DNA (1 μg) was digested with HindIII. After digestion, samples were extracted with phenol/chloroform and DNA was precipitated with ethanol. Precipitated DNA was diluted to 1 μg/ml in ligase buffer (50 mM Tris-HCl pH 7.6, 10 mM MgCl$_2$, 1 mM ATP, 1 mM DTT), and incubated with 2.8 Weiss Units of T4 DNA ligase at 14° C. for 20 hrs. After ligation, samples were extracted once with phenol/chloroform and DNA was precipitated with ethanol. Precipitated DNA was resuspended in 30 μl of distilled H$_2$O, then nicks were introduced by heating at 95° C. for 10 min. The regions encompassing IRF-1 exon 1 and intron 1 were amplified in the PCR reaction (DNA thermal cycler, Perkin-Elmer Cetus) using the primers and orientations indicated in FIG. 5. The reaction was carried out (95° C. for 30 sec., 60° C. 1 min., 70° C. 2 min., 40 cycles) in 50 μl volumes with 1 mM MgCl$_2$, 0.01% gelatin, and 1.25 U Taq DNA polymerase (Perkin-Elmer Cetus). PCR products were checked by agarose gel electrophoresis, and the appropriate bands (as indicated in FIG. 5) were eluted from the gel. The recovered DNA fragments were cloned into pBluescript; 6 independently isolated clones were sequenced.

This procedure was repeated for the other exon and intron of the IRF-1 gene.

FIG. 5B shows the sequence of the cloned PCR product derived from the leukemic sample (P, Sample 10) and from normal DNA (N). It will be seen that the sequence of the leukemic sample diverges 10 nucleotides after primer 1 in intron 1.

The expected 1.1 kb band was detected in normal DNA while an additional smaller band of approximately 500 bp was noted in the leukemic patient sample. As shown in FIG. 5, the DNA sequence upstream of the BglII site in intron 1 in the leukemic sample diverged from the normal IRF-I sequence 10 nucleotides after the primer 1 DNA sequence. No divergence in sequence between normal and leukemic cell DNA was observed downstream of the primer 2 sequence, corresponding to exon 2. These results confirm the rearrangement of the IRF-1 gene in the leukemic sample, resulting in loss of exon I and the IRF-1 promoter region.

These results indicate that one allele of the IRF-1 gene has likely been inactivated in the majority of leukemic cells in Sample 10 by a deletion of the promoter region and a portion of exon 1. Southern blot analysis (FIG. 4B), dual color FISH studies, and the cytogenetic detection of a del(5)(q13q33) all imply that the residual IRF-1 allele has been deleted in a significant population of these leukemic cells. Therefore, both IRF-1 alleles were inactivated in a significant number of cells in this leukemic patient, one by a large interstitial deletion involving one chromosome 5q and one by an inactivating rearrangement in the second IRF-1 allele that disrupted the IRF-promoter region and exon 1.

EXAMPLE 6 mRNA expression levels of IRF-1 and IRF-2 during the cell cycle of mouse NIH3T3 cells were examined. NIH3T3 cells were initially maintained in Dulbecco's modified Eagle's medium (DMEM) containing 10% fetal calf serum (FCS). The cells were grown to confluency and initially arrested by serum starvation in serum-free DMEM for 24 hrs (G1 arrest), then induced to transit the cell cycle by addition of DMEM supplemented by 10% FCS and harvested at appropriate times after stimulation. The incorporation of $^3$H-thymidine into DNA was measured by pulse labelling cells ($2\times10^4$) with 5 $\mu$Ci$^3$-thymidine (2.0 Ci/mmol) for 1 hour at indicated times (see FIG. 6A) after serum stimulation as described by Mudryj et al., *EMBO J.* 9: 2179–2184 (1990).

Figure 6A:
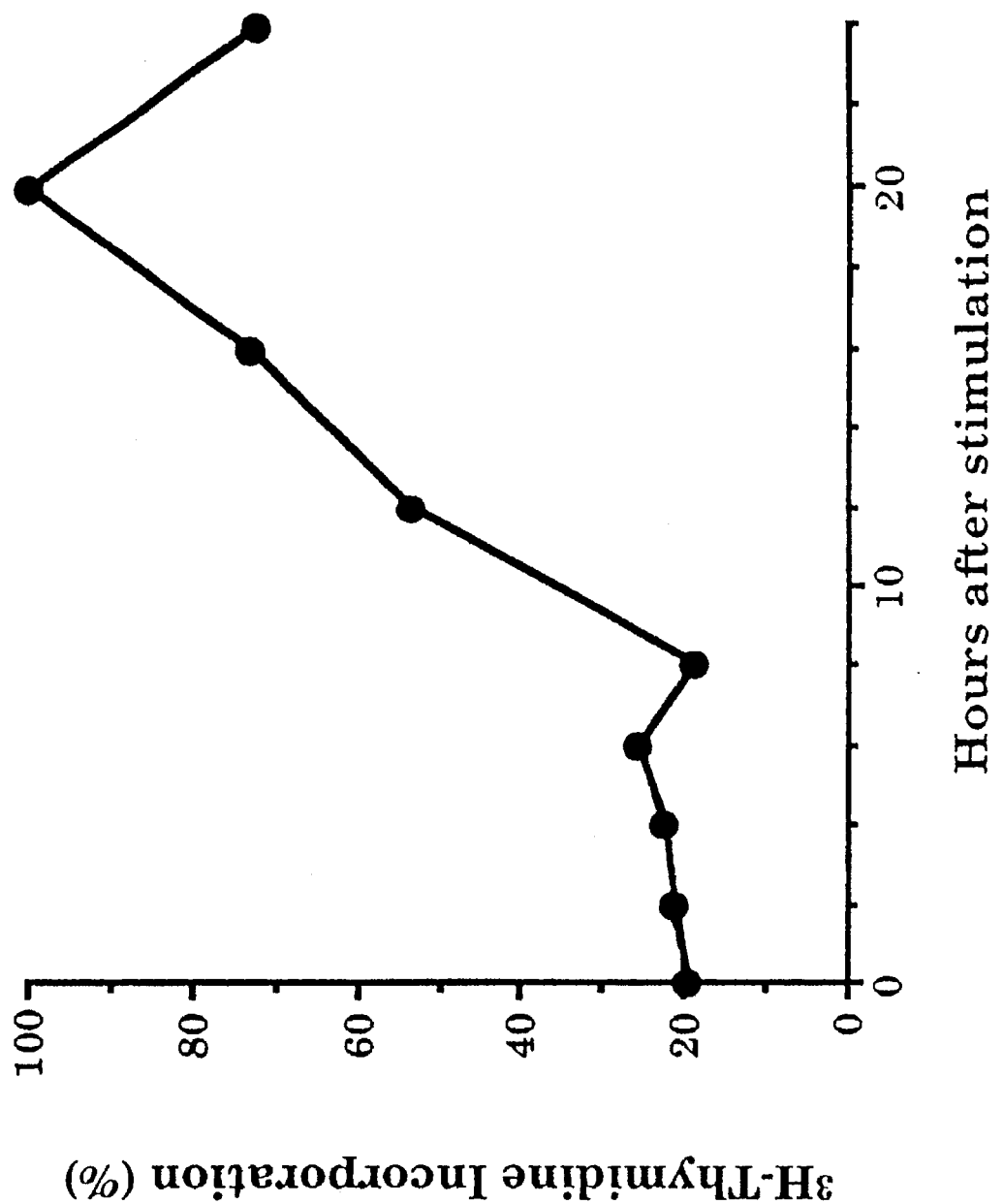

As shown in FIG. 6A, $^3$H-thymidine uptake assay revealed that DNA synthesis began 8–12 hrs after serum stimulation. Flow cytometric analysis of the cell cycle also revealed that the cells in fact entered S phase during this period. Total RNAs were isolated periodically and 10 µg subjected to S1 mapping analysis of IRF-1 and IRF-2 mRNAs (as described in Fujita et al., *Cell* 49: 357–367 (1987)). The mouse IRF probes (FIG. 6B) were the same as described in Harada et al., ibid. (1990) (specific activity 3. $1\times10^6$ cpm/pmol for IRF-1, $3.0\times10^6$ cpm/pmol for IRF-2). The human IRF-1 probe DNA is a 143 nucleotide probe which encompasses nucleotide residues −46 to +97 (relative to the major cap site at +1) of the human IRF-1 gene (specific activity, $4.7\times10^6$ cpm/pmol).

Figure 6B:
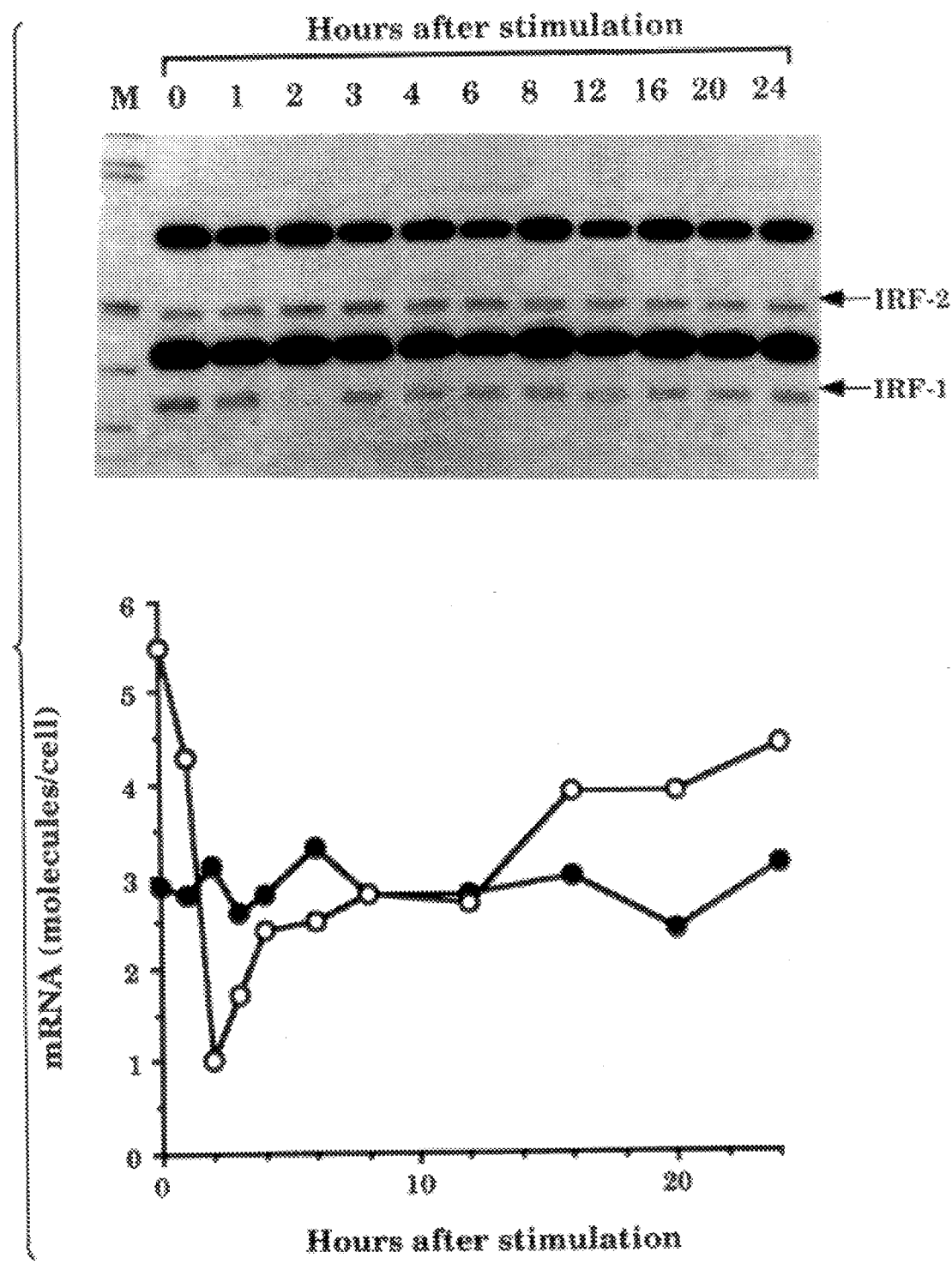

As shown in FIG. 6B, IRF-1 mRNA expression is observed at its highest levels (only about 5 copies/cell) in growth-arrested cells and declines sharply following serum stimulation. In fact, IRF-1 mRNA was found to reach a level about 5 fold lower than that of growth arrested cells 2 hrs. after stimulation, and then increase gradually, beginning prior to the onset of DNA synthesis (FIG. 6B). In contrast, the expression levels of IRF-2 mRNA remained essentially constant throughout the cell cycle. The mRNA copy number was determined by the method described in Harado et at., *Cell*, ibid. (1989) and Fujita et al., *Cell*, ibid. (1987).

Western blotting analysis of cell extracts by anti-IRF-1 antibodies also revealed an oscillation of IRF-1 levels during the cell cycle.

Figure 6C:
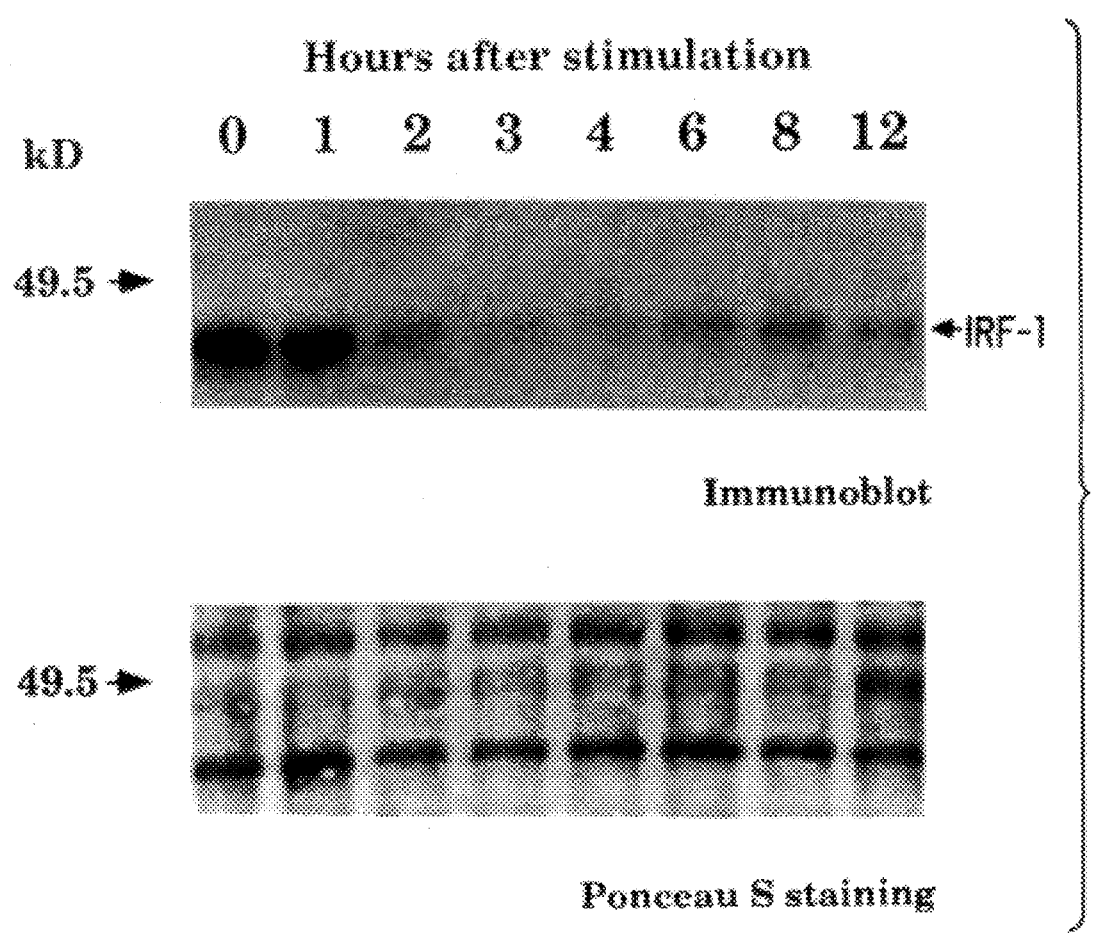

The Western blot analysis was carried out at the indicated times as follows:

Whole cell extracts were prepared at the times indicated in FIG. 6C by lysing $5\times10^5$ cells for 20 min. at 4° C. with lysis buffer [50 mM Hepes-NaOH (pH 7.0), 0.1% Nonidet P-40, 250 mM NaCl, 100 mM NaF, 200 µM Na$_3$VO$_4$, 10 µg/ml each of aprotinin, PMSF, and leupeptin] at a volume $2.5\times10^6$ cells/50 µl. Following centrifugation at 4° C. for 20 min., the extracts were subjected to 12.5% SDS-PAGE analysis. The proteins were then electrophoretically transferred to PVDF membrane filter and stained with Ponceau S non-specific dye (Harlow and Lane (1988)). Immunodetection was carried out as described by Hatakeyama et al., *Science* 252: 1523–1528 (1991) with the cocktail of anti-mouse IRF-1 monoclonal antibodies TK-1 and TK-3 (10 µg/ml each in TBST milk).

IRF-1 expression was found to culminate in the growth arrested stage, and drop approximately 6 fold 3 hrs after serum restoration, then subsequently increase again (FIG. 6C). These results thus indicate an oscillation of the IRF-1/IRF-2 ratio during the cell cycle. Similar observations were made in an interleukin 3 (IL 3) dependent hematopoietic cell line, BAF-D03.

EXAMPLE 7

The effect of perturbing IRF-1/IRF-2 ratio on cell growth was examined by generating NIH3T3 cell clones in which IRF-2 is overexpressed. The plasmid pact-2 (Harada et al., ibid. (1990)), in which the murine IRF-2 cDNA is expressed from the chicken D-actin promoter, was co-transfected with a neo-resistance gene, pSTneoB (Kato et al., *Mol. Cell. Bid.* 10(2): 486–491 (1990)), into the NIH3T3 cells ($5\times10^5$ cells/10 cm dish) by calcium phosphate method (Fujiha et al., *Cell* 41: 489–496 (1985)). The transfected cells were then maintained in selection media containing 700 µg/ml G418 the day following transfection. G418-resistant colonies were isolated after 2–3 weeks. Control cell lines were derived from transfection of NIH3T3 cells with the parental vector, pAct-C (Harada et al., ibid. (1990)).

Figure 7A:
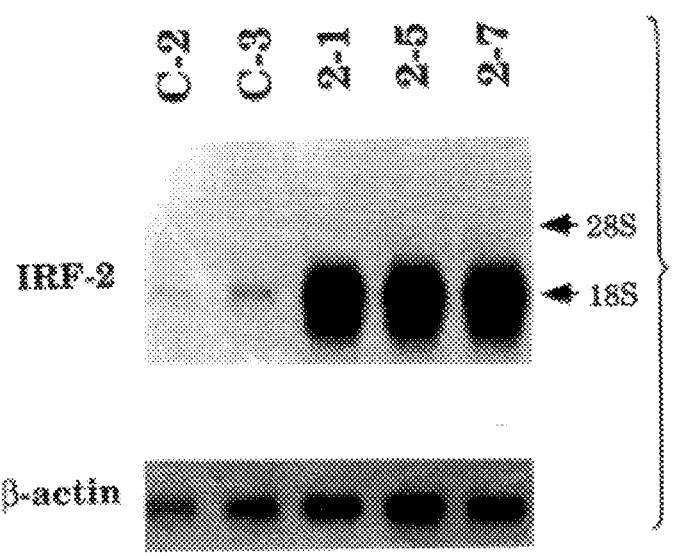
Figure 7B:
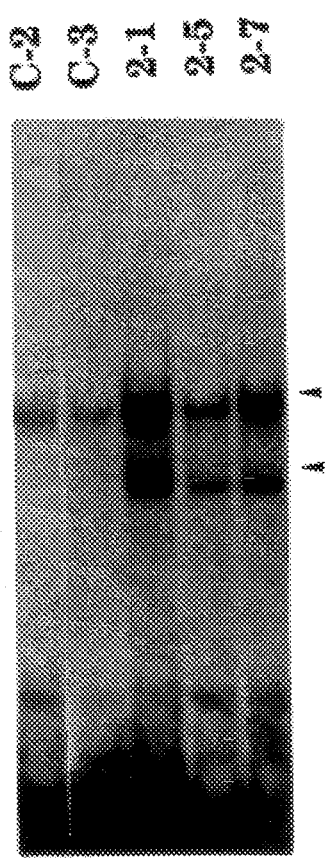

After this selecting for neo-resistance, several clones were obtained which express high levels of IRF-2 mRNA. Three cell clones, 1-2, 2-5 and 2-7, were arbitrarily chosen for further analysis in which 5 µg of RNA were subjected to Northern blot analysis using a mouse IRF-2 cDNA and a human β-actin pseudogene respectively as probes. The expression levels of IRF-2 mRNA in these clones were about 40 times above the basal expression levels observed in the pAct-C transfected control cell clones (C-2, C-3) (FIG. 7A). However, when assayed by gel-shift analysis, (using the method described in Harada et al., ibid. (1990)), it was found that IRF-2 protein levels in clones 2-1, 2-5 and 2-7 were only 9, 4 and 7 fold higher than those observed in the control cells, respectively (FIG. 7B), implying that the IRF-2 expression may be down-regulated post-transcriptionally. The gel shift analysis was carried out using 5 fmol of the $^{32}$P-labelled C13 oligomer as the probe (specific activity 5000 cpm/fmol) and whole cell extracts from $2\times10^4$ cells. Although cells overexpressing IRF-2 did not exhibit any obvious morphological changes, they displayed marked differences in other growth properties. The cells were seeded at $2\times10^4$ cells per 35 mm plate, grown in DMEM supplemented with 10% FCS and 700 µg/ml G418 and counted on the indicated days with a coulter counter. As shown in FIG. 7C, the 2-1, 2-5 and 2-7 cell clones grew at the same rate as the controls, but reached a higher cell density (about three fold). Furthermore, all of these clones displayed anchorage-independent growth. The colony forming assay was performed essentially as described by Miyashita and Kanunago, *Cell* 5: 131–138 (1975). In this procedure 10⁵ cells were suspended with 1.3% methyl cellulose gel dissolved in culture medium and overlayed on an agarose bed composed of 53% agarose and culture medium colonies were scored 3 weeks after seeding. The efficiency of colony formation in the methyl cellulose gel was 6-15%, whereas no colony formation was seen with the control clones (Table 2). It is known that these properties often correlate with malignant transformation (Freedman and Shin, Cell 3: 355-359 (1974); Keath et at., Cell 39: 339-348 (1984)).

EXAMPLE 8

The tumorigenic potential of the cells overexpressing IRF-2 was investigated. Cells ($2 \times 10^6$) from the three clones 2-1, 2-5 and 2-7 resuspended in 200 µl of DMEM without FCS (Shin, Meth. Enzymol. 58: 370-379 (1979)) were injected subcutaneously into 4-6 week old nude mice (Balb/c nu/nu; Clea Japan, Inc.) on both flanks. Cells were scored as tumorigenic if a visible nodule appeared at the site of injection and increased thereafter. Tumors developed within a relatively short latent period (2-3 weeks; Table 2) continuing to grow unrestricted, although they showed no sign of metastasis. Mice that did not develop tumors were observed for 6 weeks. No tumors developed in nude mice injected with cells from the control clones C-2 and C-3 during the same time period. This entire round of IRF-2 cDNA transfections and assays was repeated three times and the results were reproducible; in each experiment, clones overexpressing IRF-2 showed altered growth properties and tumorigenic potential (12 clones in total). Furthermore, essentially the same level of IRF-2 mRNA expression and the same growth properties were observed in the cells recovered from the tumors generated in the nude mice. Taken together, these results show clearly that the altered growth properties and tumorigenicity of the 2-1, 2-5 and 2-7 cells are caused by the elevated expression of the transcriptional repressor IRF-2.

EXAMPLE 9

Reversal of the IRF-2 induced transformation by IRF-1

The above examples demonstrate an oncogenic propensity of IRF-2, and that the maintenance of a balance between IRF-1 and IRF-2 expression is important in maintaining normal restraints on cell growth. When this balance is perturbed by the overexpression of IRF-1 cell proliferation may by inhibited (Yamada et al., ibid. (1991)), whereas the overexpression of IRF-2 may promote unrestrained growth, as shown above. This example shows that the transformed phenotype displayed by NIH3T3 cells overexpressing IRF-2 could be reverted to the original phenotype by increasing the expression level of IRF-1 and thus restoring the IRF-1/IRF-2 ratio to a "normal" range. To this end, a 1 kb DNA segment containing all ten exons, as well as the promoter region (455 bp from the major cap site, see Yamada et al., ibid. (1991)) of the human IRF-1 gene was introduced into the IRF-2 transformed cells. In view of the previously mentioned results which indicate the importance of regulated IRF-1 gene expression during the cell cycle (FIG. 6), the genomic IRF-1 clone was used in this experiment in order to ensure that expression of the ectopic IRF-1 gene was synchronized with that of the endogenous gene.

To obtain the cell clones which express an elevated level of IRF-1, fifteen micrograms of the plasmid, pUCHIRF1B (the 19 kb human IRF-1 gene subcloned into EcoRI site of pUC19) were co-transfected with pMiwhgh (0.3 µg) into 2-1, 2-5 or 2-7 cells ($5 \times 10^5$ cells/10 cm dish) by the calcium phosphate method. Plates were fed and maintained in selection media containing 100 µg/ml hygromycin the day following transfection. Hygromycin-resistant colonies were isolated after 2-3 weeks.

The 2-1, 2-5 and 2-7 cell lines which were co-transfected with the IRF-1 gene and a hygromycin (hgr) resistance gene, pMIwhgH (Kato et al., Mol. Cell. Biol. 10(2): 486-491 (1990))and hygromycin-resistant clones were selected and subsequently screened for the stable integration of the human IRF-1 gene. The transfectants 2-1-1, 2-1-2, 2-5-1, 2-7-3 and 2-7-4 were derived from the respective parental clones 2-1, 2-5 and 2-7. Human IRF-1 mRNA expression was examined by S1 mapping analysis as described above. As summarized in Table 3, the steady-state IRF-1 mRNA expression levels in these clones varied in the following order, from highest to lowest; 2-5-2, 2-7-3, 2-7-4, 2-1-1 and 2-1-2.

Figure 8A:
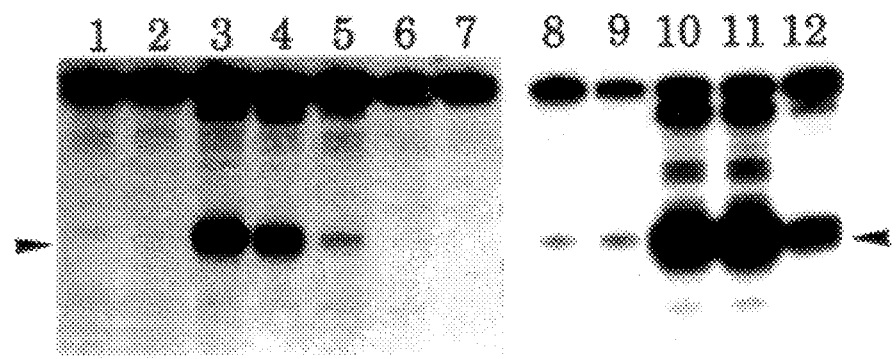

The hygromycin-resistant clones were mock-induced or induced by NDV (Newcastle Disease Virus) as previously described (Fujita et al. (1985)). The transfected IRF-1 gene was virus-inducible in all clones (Table 3) and, in a separate set of experiments, it was shown that the promoter sequence within the cloned gene is also IFN-inducible (Itoh, Genomics 10: 1092-1099 (1990)). 9 hours after induction or mock-induction total RNA was isolated and 5 µg of RNA were subjected to S1 mapping analysis using the procedure described above. The results are shown in FIG. 8A, in which the Lanes are identified as follows: Lanes 1-7, mock-induced; Lanes 8-12 NDV-induced; Lanes 1 and 8, cell line 2-1-1; Lanes 2 and 9, 2-1-2; Lanes 3 and 10, 2-5-2; Lanes 4 and 11, 2-7-3;, Lanes 5 and 12, 2-7-4; Lane 6, C3; Lane 7, 2-7. The arrow heads indicate the positions of the protected human IRF-1 probe. IRF-1 and IRF-2 activity was demonstrated by gel shift analysis in clones 2-7-3 and 2-7-4 carried out according to the procedure of Harada et al., ibid. (1990).

Figure 8B:
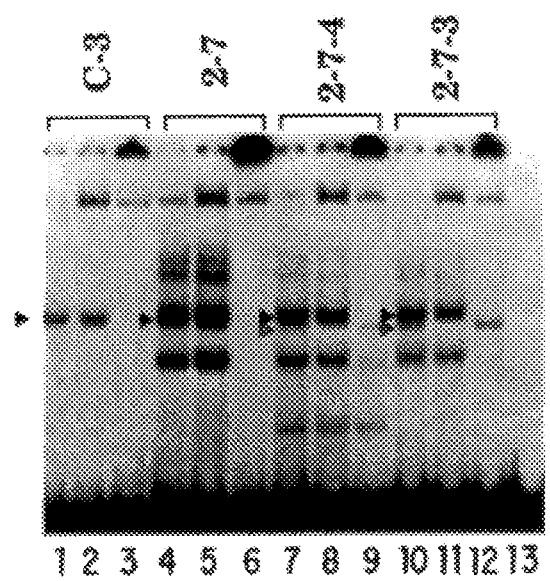

This procedure was carried out using 5 fmol of the ³²P-labelled C1 oligomer as the probe (specific activity 5000 cpm/fmol) and whole cell extracts from $5 \times 10^4$ cells. The C1 oligomer consists of four repeats of the sequence AAGTGA and contains two IRF binding sites. This oligomer was used instead of the C13 oligomer since it is easier to delete the IRF-1 activity (Watanabe et al., Nucl. Acids Res. 19: 4421-4428 (1991)). The results are shown in FIG. 8B in which Lanes 1, 4, 7 and 10 had 2 µl of non-immune rabbit serum included in the reaction mixture; Lanes 2, 5, 8 and 11 had 2 of rabbit anti-mouse IRF-1 antiserum included; Lanes 3, 6, 9 and 12 had 2 µl of rabbit antimouse IRF-1 antiserum included; and Lane 13 had no extract. Open and closed triangles indicate positions of the factor-DNA complexes of IRF-1 and IRF-2 respectively. The endogenous murine IRF-1 activity became detectable in Lane 3 and 6 only after prolonged exposure. Faster migrating bands probably represent the breakdown products of IRF-1 and/or IRF-2 bound to the DNA probe. Slower migrating bands in Lanes 4, 5, 7, 8, 10 and 11 represent the DNA probe bound by two IRF-2 molecules.

The expression of IRF-2 mRNA was determined by subjecting 5 µg RNA to Northern blot analysis. The RNA was isolated as described above. The probe DNAs were labelled by the random primer method (Amersham) and were a 1.4 kb XbaI cDNA fragment from pact-2 for mouse IRF-2 (Harada et at., ibid. (1990)) and a 2.0 kb BamHI-PvuII fragment of λHa-204 (Myamoto et al., ibid. (1988)) for human/5-actin (human/5-actin pseudogene).

Figure 8C:
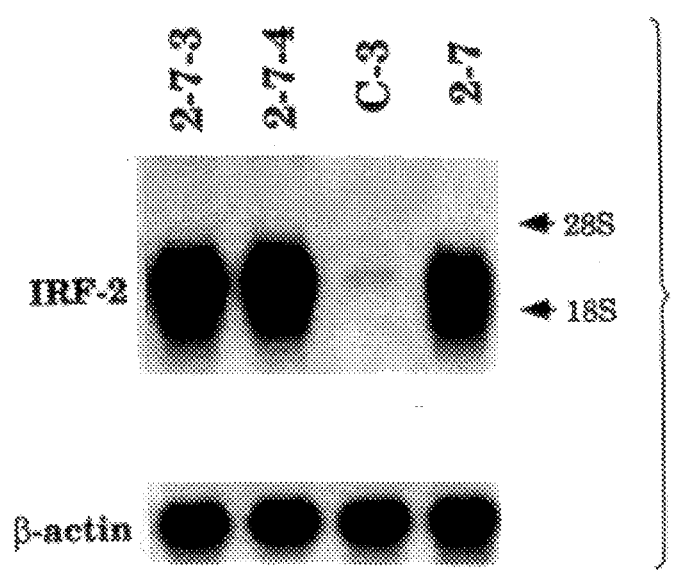

IRF-2 mRNA expression levels in all of these clones was found to be the same as in the parental cells as can be seen in FIG. 8C. Interestingly, the gel-shift assay data shown in FIG. 8B indicate that the DNA binding activity of IRF-2 in those clones is somewhat reduced as a result of ectopic IRF-1 expression, raising the possibility that IRF-1 may affect IRF-2 activity post-transcriptionally. A similar observation was made with clone 2-5-2.

The tumorigenic properties of those cells were strongly suppressed. In fact, the efficiency with which tumorigenicity was suppressed correlated with the levels of ectopic IRF-1 mRNA expression; clones 2-5-2 and 2-7-3, both of which express the human IRF-1 mRNA at higher levels, showed very strong suppression, clones 2-7-4 and 2-1-1 in which the mRNA expression levels are relatively lower, showed somewhat weaker suppression, while clone 2-1-2 showed no suppression (Table 3). Concomitant with the loss or reduction of the transformed phenotype, the 2-7-3 and 2-7-4 cell clones exhibited a loss or reduction, respectively, of other transformation-associated traits, such as increased cell saturation density (FIG. 8D) and anchorage-independent growth (Table 3). Thus, the IRF-2-induced transformation of NIH3T3 cells is reversible by the introduction and increased expression of the IRF-1 gene.

The IRF-IFN System in Growth Control and Tumorigenesis

As shown herein, subtle changes in the ratio of the transcriptional activator IRF-1 and its structurally-related transcriptional repressor IRF-2 can have profound effects on cell growth. IRF-1 exhibits anti-oncogenic properties while in contrast, overexpression of IRF-2 promotes tumorigenesis. Recent studies in which IRF-1 antisense oligomers were shown to block differentiation in a myeloid leukemia cell line (Abdollahi et al., Cell Growth Differ. 2: 401–407 (1991)) and our preliminary observation that expression of IRF-1 antisense mRNA in NIH3T3 cells produces a similar phenotype to that seen with IRF-2 overexpression are also consistent with the idea that IRF-1 is a tumor suppressor gene. IRF-1 and IRF-2 were first discovered as transcriptional regulators of the type I IFN genes (Miyamoto et al., ibid. (1988); Fujita et al., ibid. (1989); Harada et al., ibid. (1989)) and were subsequently shown to regulate the expression of IFN-inducible genes (Harada et al., ibid. (1990); Reis et al., ibid. (1992)). In fact, IRF-1 is IFN-inducible. The type I IFNs inhibit cellular proliferation in normal and transformed cells (Einat et al., Nature 313: 597–600 (1985); Linet al., Science 233: 356–359 (1986)) and induction of IFN expression in hematopoietic cells inhibits cellular proliferation in an autocrine fashion (Moore et al., Science 233: 171–181 (1984); Resnitzky et al., Cell 46: 31–40 (1956)). Furthermore, hemizygous and homozygous deletions of either the IFN-β gene or the IFN-α gene cluster have been reported in acute lymphoblastic leukemia patients with deletions of chromosome 9q22 (Diaz et al., Proc. Natl. Acad. Sci. USA 85: 5259–5263 (1988), N. Engl. J. Med. 332: 77–82 (1990)), suggesting that loss of IFNs may disrupt normal growth control mechanisms and promote leukemogenesis (Grander et al., Blood 79: 2076–2083 (1992)). The present invention makes use of our discoveries that IRF-1 is one of the critical targets of the IFNs, including the expression of target genes in a cascade that is critical for the inhibition of cell growth and that subtle changes in the IRF-1/IRF-2 ratio may perturb cell growth and promote leukemogenesis.

The Chromosome 5q31 Region and del(5q)

Very recent physical mapping studies of 5q31 indicate that IRF-1 lies between the IL-4/IL-5 and IL-3/GM-CSF gene clusters and that IL-4 and IRF-1 are both present in a 450 kb YAC; IL-9 and EGR-1 are 1–2 Mb telomeric to this region (Warrington et al., Genomics 13: 803–808 (1992)). However, as discussed above, none of the genes that were previously mapped to this region appears to fulfill the requirements expected of a candidate tumor suppressor gene (see also Nimer and Golde, ibid. (1987)) and for each of these genes, no functional proof has yet been provided for a tumor suppressor gene role. A CDC25 homologue (CDC25C) to 5q31.1 (M. P. T. Meeker, UCSE, Sartor et al., Genomics 13: 991–913 (1992)) was recently mapped and IRF-1 and CDC25C were co-localized to a 175 kb pulsed-field gel fragment.

Furthermore, CDC25C was not deleted in all del 5(q) cases that contained IRF-1 deletions and CDC25C was not deleted in case 10 (Table 1) which had a deletion of IRF-1 encompassing only exon 1 and the promoter region. These studies further indicate that it is IRF-1 that is the critically deleted tumor suppressor gene in these syndromes.

The variability observed in the proximal (5q13–15) and distal (5q31–33) breakpoints in the del(5q) in individual patients and the occurrence of variants such as del(5) (q31q35) have suggested that these precise locations of the breakpoints in the del(5q) is not critical, as long as the 5q31 region is deleted. CSF1R (EMS) maps to 5q33.1 and may be hemizygously deleted in cases of del(5q) with distal breakpoints involving 5q33-q35 (Nienhuis et al., Cell 42: 421–428 (1985); Le Beau et at., ibid. (1986)); although homozygous deletions of the CSF1R were recently reported in some MDS patients (Boultwood et al., Proc. Natl. Acad. Sci. USA 88: 6176–6180 (1991)), these findings have not been confirmed. The dual color FISH results herein indicate that the precise location of the del(5q) breakpoints may not be critical in the pathogenesis of MDS. Even within an individual MDS patient, distinct clonal populations of cells could be identified that contained different proximal breakpoints on 5q; however, all of these clones had deleted the 5q31 region and the IRF-1 allele. Our FISH studies also indicate that there is a significant and heterogeneous loss of DNA, including the IRF-1 allele, at the breakpoint site in the translocation 5q31 in different AML patients. These findings are in contrast to previous cytogenetic studies that had indicated that translocations involving 5q31 were likely to be balanced reciprocal translocations (Fourth International Workshop on Chromosomes in Leukemia, 1982).

The Significance of Hemizygous Deletion of IRF-1

In the original tumor suppressor gene model developed from studies of retinoblastoma (RB), tumorigenesis resulted from a loss of function of both alleles of a tumor suppressor gene (reviewed in Marshall, ibid. (1991)). Loss or inactivation of a single allele, although a predisposing condition for tumorigenesis, was not thought to have significant biologic consequences. However, more recent studies in other human tumor models indicate that loss of one allele of a tumor suppressor gene may have quite significant biologic effects and in some instances be sufficient to promote tumorigenesis. Although homozygous deletions of the WT1 locus at 11p13 occur in Wilms' tumor, one example was discovered in which the candidate WT1 gene had undergone a small internal deletion (Haber et al., Cell 61: 1257–1269 (1990)). The residual WT1 allele was normal in this case, suggesting that a single mutant allele at 11p13 could promote Wilms' tumorigenesis particularly if mutations were sustained at other loci such as 11p15 (Haber et al., ibid. (1990)). Similarly, loss or inactivation of one NF1 allele in neurofibromatosis may be sufficient to induce benign neurofibromas (Liet at., ibid. (1992)) and deletion or inactivation of one APC allele may promote the development of colorectal adenomas (Vogelstein et al., *N. Engl. J. Med.* 319: 525–532 (1988); Groden et al., ibid. (1991)). Tumor progression in both of these models is associated with the acquisition of mutations at other proto-oncogene and tumor suppressor gene loci (reviewed in Marshall, ibid. (1991)). Recent studies of p53 have also demonstrated that mice heterozygous for a null p53 allele develop tumors, albeit rarely, while mice homozygous for a null p53 allele develop a variety of tumors at an early age (Donehower et al., *Nature* 356: 215–221 (1992)). Collectively, these studies suggest that loss of a single allele of certain tumor suppressor genes may promote the expansion of a clone of altered cells thereby creating a target population for further genetic mutations.

It has been shown herein how the loss of a single IRF-1 allele may also be biologically significant. Loss or inactivation of a single IRF-1 allele may decrease IRF-1 expression enough to diminish the IRF-1/IRF-2 ratio, thereby perturbing cell growth. In this context, the IRF-2 gene was examined in leukemia and MDS samples and amplification, deletion, or structural rearrangements of IRF-2 was not detected in any sample by Southern blot analysis. Thus, the loss of a single IRF-1 allele could result in abnormalities in the IRF-1/IRF-2 ratio in leukemia and MDS with del(5q).

A clone of cells that had lost only a single IRF-1 allele would be expected to have slow capacity for expansion and be predisposed to further genetic mutations. Interestingly, these more indolent biologic characteristics are observed in the majority of patients with the 5q-Syndrome (Van den Berghe et al., ibid. (1974), ibid. (1985); Dewald et al., ibid. (1985)). Females with refractory anemia and del(5) (q13q33), the most frequent type of interstitial deletion, have an indolent clinical course, a low probability of acquiring further cytogenetic abnormalities, and a low transformation rate to AML (Dewald et al., ibid. (1985); Van den Berghe et at., ibid. (1985); Nimer and Gold, ibid. (1987)). In contrast, the presence of additional cytogenetic abnormalities at diagnosis or their acquisition during the course of the disease, and, male sex are associated with higher frequencies of leukemic transformation (Nimer and Gold, ibid. (1987)). These findings indicate that although loss of one IRF-1 allele may promote tumorigenesis, it is the loss of an additional IRF-1 allele in a subpopulation of blasts and/or the acquisition of mutations at other genetic loci that are necessary for full leukemic transformation as demonstrated by the cytogenetic and molecular findings in the leukemia and MDS patients described herein. All del(5q) patients with preleukemic myelodysplastic syndromes had hemizygous deletions of IRF-1. Loss of one IRF-1 allele was also seen in each sample of de novo AML with del(5q) although each case had acquired extensive cytogenetic abnormalities at other loci at the time of disease presentation. Interestingly, both cases with homozygous deletions of IRF-1 detected in a subpopulation of blasts were acute leukemias: a case of AML arising from antecedent MDS and a case of ALL. No mutations which would alter IRF-1 structure were detected in the residual IRF-1 allele in the patients reported here.

In summary, the diagnosis carried out on the patients described above shows that loss of one IRF-1 allele may be a prerequisite event for the expansion of a preleukemic clone which may then progress to leukemia through the loss of the second IRF-1 allele or by sustaining further genetic mutations at other loci.

Regulation of the IRF genes in cell growth

It has been shown previously that expression of IRF-1 gene is induced transiently by viruses, IFNs and some other cytokines (Fujita et al., *Proc. Natl. Acad. Sci. USA.* 86: 9936–9940 (1989); Harada et al., ibid. (1989); Pine et al., *Cell Biol.* 10: 2448–2457 (1990); Yu-Lee et al., *Mol. Cell. Biol.* 10: 3087–3094 (1990)). The foregoing examples indicate that in normally growing cells this gene is also subject to regulation during the cell cycle. In cells, e.g. NIH3T3, IRF-1 gene expression is at its highest when cells are in a growth-arrested state, drops sharply upon resumption of growth following serum stimulation and then gradually increases until cells enter the S phase. Presumably, overexpression of IRF-2 in the NIH3T3 cell line described here suppresses the cell growth-restraining function of IRF-1. However, such suppression might be critical for altering cell growth only at a certain stage(s) of the cell cycle. IRF-2 overexpression does not alter the serum dependent property of these cells and they still become growth-arrested upon serum starvation. Hence, it is possible that the "critical" stage(s) at which IRF-2 suppresses the IRF-1 function may occur after the cells have entered the cell cycle.

A link between the IFN system and cell growth control

Previously, it has been shown that IRF-1 is a transcriptional activator, playing a critical role in the expression of type I IFN and IFN-inducible genes, and that IRF-2 represses the action of IRF-1 by competing for binding to the same DNA cis-elements (Fujita et al., ibid. (1989); Harada et al., ibid. (1990); Näf et at., ibid.. (1991); Au et al., ibid. (1992); Reis et at., ibid. (1992); Stark and Kerr, ibid. (1992)). In virally infected cells, IRF-1 must undergo some type of modification(s) for the efficient activation of the IFN genes (Watanabe et al., ibid. (1991)). The results described herein indicate the involvement of the IRF genes in the regulation of both the IFN system and cell growth. The abrupt induction of IRF-1 gene by IFNs in normally growing cells is responsible, at least in part, for the perturbation of the cell cycle caused by IFNs (Sokawa et at., *Nature* 268: 236–238 (1977); Balkwill and Taylor-Papdimitriou, *Nature* 274: 798–800 (1978)).

The effect of IRF-1 may be influenced by the expression level of IRF-2, the latter of which is expected to vary in different cell types.

Possible mechanism of the IRF-1-induced cell growth regulation

In view of the results described herein it may be inferred that IRF-1 activates a set of genes whose products are required for the negative regulation of cell growth. The expression of such genes may be critical for the normal regulation of cell growth, since it is assumed that IRF-2 induces the transformation of cells by repressing the function of IRF-1. This assumption is supported by the observation that expression of IRF-1 reverses the transformed phenotype induced by IRF-2. Previously, it has been demonstrated that many if not all of the IFN-inducible genes contain sequences within their promoter regions which bind IRFs (reviewed by Vilcek, ibid. (1990); Stark and Kerr, ibid. (1992)). In this regard, evidence has been provided showing that the 2'-5'-oligoadenylate synthetase, whose gene is IFN-inducible, is involved in the inhibition of cell proliferation, although there have been some conflicting reports concerning this point (reviewed by Revel and Chebath, *Trends Biol. Sci.* 11: 166–170 (1986); De Maeyer and De Maeyer-Guignard, ibid. (1988)). Interestingly, the activity of this enzyme appears to fluctuate with the cell cycle (Jacobsen et al., *Proc. Natl. Acad. Sci. USA* 80: 4954–4958 (1983); Wells and Mallucci, *Exp. Cell Res.* 159: 27–36 (1985)), and its expression is regulated by IRF-1 (Au et al. (1992); Reis et al. (1992)). On the other hand, it is possible that IRF-1 mediates its action through more than one mechanism and that the particular mechanism critical for growth regulation may very depending on cell types or cell conditions. It is unlikely that overexpression of IRF-2 causes oncogenic transformation by a mechanism(s) other than the repression of the IRF-1 function especially in view of results indicating that a phenotype similar to that induced by IRF-2 overexpression is also induced by expressing an IRF-1 anti-sense RNA in NIH3T3 cells.

Thus, IRF-1 and IRF-2 normally function as critical regulators for cell growth, and cytokines transiently induce an alteration in the balance between these two factors. In virally-infected cells, these factors are utilized to efficiently turn on the IFN-α and -β genes-an event critical to the host defense against viral invasion.

IRF-1 and other nuclear factors as tumor suppressors

The results presented show that IRF-1 is a new member of the emerging group of tumor suppressors (reviewed by Marshall, ibid. (1991); Weinberg, Science 254: 1138–1146 (1991)). So far, three nuclear factors have been extensively studied in context of tumor suppression; p105-RB (pRB) (reviewed by Weinberg, ibid. (1991); Hamel et al., Trends Genet. 8: 180–185 (1992)), p53 (reviewed by Hollstein et al., Science 253: 49–52 (1991); Levine et al., Nature 351: 453–456 (1991)) and the WT1 gene product (reviewed by Haber and Housman, Cancer Res. 59: 41–68 (1992); van Heyningen and Hastie, Trends Genet. 8: 16–21 (1992)). It appears that the latter two factors directly modulate transcriptional activities either in a positive manner (p53) (Farmer et al., Nature 358: 83–85 (1992); Kern et al., Science 256: 827–830 (1992)) or in a negative manner (WT1) (Madden et al., Science 253: 1550–1553 (1991)).

IRF-1 appears to be analogous to the well-characterized tumor suppressor, p53, in that both function as transcriptional activators and both regulate cell growth. It is intriguing that p53 levels also rise during growth arrest (Kastan et al., Cancer Res. 51: 6304–6311 (1991)), and are regulated throughout the cell cycle (Reich and Levine, Nature 308: 199–201 (1984)), as was observed in the case of IRF-1. It is also interesting that mutated oncogenic forms of p53 antagonize the function of wild-type p53 (Kern et al., ibid. (1992)), similar to the effect of IRF-2 on IRF-1. In this regard, an interesting possibility may be that p53 also has a natural antagonistic factor like IRF-2, and in fact one such candidate has been reported recently (Momand et al., Cell 69: 1237–1245 (1992); Oliner et al., Nature 358: 80–83 (1992)). In a similar context, another tumor suppressor gene, WT1, encodes a protein with DNA binding potential, and recent evidence suggests that the WT1 protein may repress transcription mediated by a structurally related activator EGR-1 and/or its family of protein (Madden et al., ibid. (1991); van Heyningen and Hastie, ibid. (1992)).

Role of IRF-1 in human cancer

As described herein the human IRF-1 gene maps to chromosome 5q31 and one IRF-1 allele is deleted in each of the examined 11 cases of acute leukemia and MDS with interstitial deletions of chromosome 5q and in two cases of acute leukemia with reciprocal translocations of chromosome 5q31. In one case of acute leukemia, a rearrangement (s) in one of the IRF-1 alleles, resulting in the deletion of the proximal promoter region and first exon, was also observed. Furthermore, the remaining IRF-1 allele was found to be deleted in the majority of leukemic cells in this case. In view of the results showing that subtle changes in the IRF-1/IRF-2 ratio can cause cells to grow in an unrestrained manner, the loss of one or both IRF-1 alleles can be taken as indicating a propensity for the critical step of developing tumors, especially leukemia and MDS with 5q31 abnormalities. Thus, IRF-1 is e.g. a critically deleted gene in the 5q-Syndrome and del(5q) that frequently occur in human leukemia and MDS.

As described herein, cells lacking IRF-1 allele(s) or containing mutated or translocated allele(s) and thus which fail to respond to this negative growth factor are more prone to acquire a malignant phenotype.

Thus, IRF-1 and IRF-2 represent a unique example of two structurally-related DNA binding factors that act in a mutually-antagonistic manner demonstrating the importance of a balance of the anti-oncogenic and oncogenic factors, alteration of which may be a critical step for cell transformation.

IRF-1 being the "critically deleted" tumor suppressor gene in patients whose tumor e.g. MDS arises due to deletions or mutations or translocations of the long arm of chromosome 5 (del (5q) or translocation 5q31) the present invention provides new possibilities for the diagnosis and therapy of tumors, especially MDS and AML. Detection of IRF-1 germline (constitutive) and somatic deletions and mutations will allow:

1. more precise diagnosis and identifications of individuals who may be predisposed to the development of tumors e.g. MDS and AML;
2. more precise diagnosis and identifications of those cancer patients e.g. MDS and AML patients where disease is initiated by or results in part from IRF-1 mutations, thereby defining a unique group of MDS and AML patients who may benefit from innovative biologic therapies (see above);
3. development of a new prognostic stratification and classification scheme for MDS and AML patients based on the presence or absence of IRF-1 mutations and deletions, the presence or absence of additional karyotypic (cytogenetic) abnormalities, and other clinical features; and
4. the rational design of new biologic therapies for MDS and AML patients with IRF-1 deletions and mutations based upon our current understanding of the physiology of the IRF-1 and IRNα/β cell growth inhibitory pathways in normal eucaryotic cells. These new and innovative therapies would include:
   a) the design of therapeutic protocols that employ cytokines or other biologic factors to selectively eliminate hematopoietic cells with IRF-1 deletions and mutations or that employ cytokines to correct the physiologic defect theft results from loss of IRF-1 function;
   b) the design of therapeutic protocols that allow for the selective elimination ex vivo of human hematopoietic stem cells (HSC) containing IRF-1 deletions and mutations from the total population of HSC or which would allow for the selective expansion of normal HSC at the expense of HSC with IRF-1 deletions and mutations, thereby purging marrow or peripheral blood HSC of such defective stem cells allowing for the autologous transplantation of corrected marrow or peripheral blood HSC to MDS and AML patients; and
   c) the design of gene therapy protocols which would deliver the IRF-1 gene to human cells with IRF-1 deletions and mutations, thereby correcting the genetic and biochemical defect that arises as a result of loss of IRF-1 function.

TABLE 1

Cytometric, FISH, and Molecular Analysis of IRF-1 Deletions in Hematopoietic Neoplasms[1]

| | | | | Fluorescence in situ Chromosomel Hybridization | | | |
|---|---|---|---|---|---|---|---|
| | | | | IRF-1 Single Color | | IRF-1(5q31.1)/5q22 Dual Color | |
| Sample Disease | Karyotype[2] | Leukemic[3] Blast % | IRF-1:C9 Hybridization Ratio | # Cells Scored | IRF-1 Allele Frequency (%) | # Cells Scored | IRF-1/5q22 Allele Frequency (%) |
| I. Interstitial Deletions of Chromosome 5q | | | | | | | |
| *Myelodysplasias* | | | | | | | |
| 1 Refractory Anemia | 46,XX,del(5)(q13q33)[10]/46,XX[2] | | 0.36:1 | 1014 | 2–66.7<br>1–23.9<br>0–9.4 | | Excluded[e] |
| 2 MDS/Anemia | 46,XY,del(5)(q13q33)[3]/46,XY[22] | | 0.62:1 | 1112 | 2–71.9<br><br>1.23.6<br><br>0–4.5 | 73 | 2 5q22/2<br>IRF-1 - 37.0<br>2 5q22/1<br>IRF-1 - 20.5<br>1 5q22/1<br>IRF-1 - 31.6<br>1 5q22/2<br>IRF-1 - 8.2<br>2 5q22/0<br>IRF-1 - 2.7 |
| 3 Refractory Anemia | 45,XX,del(5)(q13q33),–6,+1(6p),del(7)(q22q22),–10,–12,+der(12)t(12;7)(p13;7) [4]/46,XX[14] | | 0.68:1 | 1001 | 2–46.0<br>1–48.3<br>0–5.7 | | N.D. |
| 4 MDS | 52,X,–Y,+1,del(5)(q13q33),+8,+9,+11,i(14q),+18,+19,+22 [15] | | 0.56:1 | N.D. | N.D. | | N.D. |
| *Secondary Leukemias* | | | | | | | |
| 5 RAEB —> AML | 40–46,XX,del(5)(q13q33)–11,+13,+16,–18,–22 [20] | 59% | 0.58:1 | 1018 | 2–8.2<br>1–84.5<br>0–7.3 | | Excluded |
| 6 RAEB —> AML | 46,XX,del(5)(q15q33) [25] | 60% | 0.58:1 | 1261 | 2–14.5<br><br>1–78.1<br><br>0–7.4 | 72 | 2 5q22/2<br>IRF-1 - 8.3<br>2 5q22/1<br>IRF-1 - 23.6<br>1 5q22/1<br>IRF-1 - 43.1<br>1 5q22/2<br>IRF-1 - 2.7<br>2 5q22/0<br>IRF-1 - 13.9<br>1 5q22/0<br>IRF-1 - 8.4 |
| *De Novo Acute Leukemias* | | | | | | | |
| 7 De Novo AML | 44,XX,del(5)(q11.2q33),del(7)(q11.2),–8,–10,+der(10)t(10;11)(q22;q13),–11,+der(11),t(11;7),(q13;7),–13,+der(13)t(13;7)(q372;7),–16[17]/44,inden,del[(6)(q715;q723) [3] | 80% | 0.35:1 | 1000 | 2–2.7<br><br>1–86.3<br><br>0–11 | 76 | 2 5q22/2<br>IRF-1 - 4.0<br>2 5q22/1<br>IRF-1 - 11.7<br>1 5q22/1<br>IRF-1 - 80.3<br>1 5q22/2<br>IRF-1 - 4.0<br>2 5q22/0<br>IRF-1 - 0.0 |
| 8 De Novo AML | 45,X,–N,der(4)t(4;7)(p16;7),del(5)(q13q33),del(8)(q21.3q24.2),del(9)(q12q32),del(17)(p11.2),drains | 80% | 0.36:1 | 1000 | 2–1.2<br>1–84.7<br>0–14.1 | | Excluded |
| 9 De Novo AML | 46,XY,del(3)(q275q277),del(5)(q272q31),del(7)(q11.2),12,+der(12)t(12;7)(p12;7)/45,iden,–7 | 90% | 0.45:1 | N.D. | N.D. | | N.D. |
| 10 De Novo AML | 46,XX,t(4;11)(q21;q23),del(5)(q15q373),[(7q),(3)/46,XX [18] | 75% | 0.55:1 | 179 | 2–55.9<br>1–25.7<br>0–18.4 | | Excluded |
| 11 De Novo AML In Relapse | 46,XY,t(2;6)(p23;q25),del(5)(q31,q35),t(8;21)(q22;q22)[13]/46,iden,t(13;18)(q14;q23) [3] | 40% | 0.81:1 | 231 | 2–67.8<br><br>1–25.7<br><br>0–6.5 | 61 | 2 5q22/2<br>IRF-1 - 44.3<br>2 5q22/1<br>IRF-1 - 36.1<br>1 5q22/1<br>IRF-1 - 9.8 |

TABLE 1-continued

Cytometric, FISH, and Molecular Analysis of IRF-1 Deletions in Hematopoietic Neoplasms[1]

| | | | | | | | Fluorescence in situ Chromosomel Hybridization |
|---|---|---|---|---|---|---|---|
| | | II. Translocations of Chromosome 5q31 | | | | | 1 5q22/2<br>IRF-1 - 4.9<br>2 5q22/0<br>IRF-1 - 4.9 |
| 12 De Novo AML | 46,XY,t(5;13)(q31;q14),−7,del(15) | | 95% | 0.46:1 | 1026 | 2–2.5 | 104 | 2 5q22/2<br>IRF-1 - 14.4 |
| | (q21q26),+21[18]/46,XY [2] | | | | | 1–87.7 | | 2 5q22/1<br>IRF-1 - 29.8 |
| | | | | | | 0–9.8 | | 1 5q22/1<br>IRF-1 - 52.9<br>1 5q22/2<br>IRF-1 - 2.0<br>2 5q22/0<br>IRF-1 - 0.9 |
| 13 De Novo AML | 46,XX,t(5;6)(q31;q21) | | 70% | 0.72:1 | 1000 | 2–2.5 | 86 | 2 5q22/2<br>IRF-1 - 6.9 |
| | | | | | | 1–77.3 | | 2 5q22/1<br>IRF-1 - 3.5 |
| | | | | | | 0–20.2 | | 1 5q22/1<br>IRF-1 - 55.9<br>1 5q22/1<br>IRF-1 - 31.4<br>2 5q22/0<br>IRF-1 - 2.3 |
| | | III. Selected Controls | | | | | |
| Hematopoietic Neoplasms with 5q Abnormalities Other Than 5q31 | | | | | | | |
| 14 MDS/CMMOL | 46,XY,t(5;12)(q33;p13),del(7)(q22q32) [20] | | | 1.02:1 | 58 | 2–84.6<br>1–15.0<br>0–0.4 | | Excluded |
| 15 Lymphoma | 46,XX,t(2;5)(q23;q35) | | | 1.06:1 | 1021 | 2–88.2 | 139 | 2 5q22/2<br>IRF-1 - 81.3 |
| | | | | | | 1–9.0 | | 2 5q22/1<br>IRF-1 - 7.9 |
| | | | | | | 0–2.8 | | 1 5q22/1<br>IRF-1 - 2.2<br>1 5q22/2<br>IRF-1 - 4.3<br>2 5q22/0<br>IRF-1 - 4.3 |
| Normal Tissues | | | | | | | |
| 16 Blood Mononuclear Cells (Cryopreserved) | 46, XY | | | 1.03:1 | 1047 | 2–89.7<br>1–8.1<br>0–2.2 | | N.D. |
| 17 Bone Marrow (Cryopreserved) | 46,XX | | | 0.92:1 | 1045 | 2–88.0 | 317 | 2 5q22/2<br>IRF-1 - 80.4 |
| | | | | | | 1–8.0 | | 2 5q22/1<br>IRF-1 - 6.3 |
| | | | | | | 0–4.0 | | 1 5q22/1<br>IRF-1 - 4.7<br>1 5q22/2<br>IRF-1 - 6.6<br>2 5q22/0<br>IRF-1 - 2.0 |

[1] Abbreviations: MDS, myelodysplasia; RAEB-->AML, refractory anemia with excess blasts in transformation to acute myeloid leukemia; AML, acute myeloid leukemia; ALL, acute lymphoid leukemia; CMMOL, chronic myelomonocytic leukemia; ND, not determined.
[2] Representative metaphase chromosome spreads were karyotyped according to standard ISCH criteria (ISCH, 1991). The number of cells identified with each clonal abnormality is given in brackets. IDEN: same as previous clone. DMINS: double minutes.
[3] The leukemia blast cell %, determined by morphologic criteria, is listed for those MDS cases in transformation to AML and each case of AML/ALL.
[4] Exclusion criteria: No 5q22 hybridization signal in >25% of cells and/or <50 hybridized cells available for analysis and scoring.

TABLE 2

Growth Properties of Cell Lines Overexpressing IRF-2 and Controls

| Cell line | Growth in methyl cellulose gel Efficiency (%) | Tumorigenicity Tumors/ injection | Latency (weeks) |
|---|---|---|---|
| C-2 | 0, 0 | 0/7 | — |
| C-3 | 0, 0 | 0/5 | — |
| 2-1 | 7, 12 | 6/6 | 2–3 |
| 2-5 | 6, 6 | 6/6 | 2–3 |
| 2-7 | 10, 19 | 6/6 | 2–3 |

Values given for growth in methyl cellulose gel are from duplicate assays. Details of the test for tumorigenicity are described in Experimental Procedures.

TABLE 3

Growth Properties of the Cell Lines Expressing Human IRF-1

| Cell line | Human IRF-1 mRNA expression (copies/cell) (NDV) − | + | Growth in methyl cellulose gel Efficiency (%) | Tumorigenicity Tumors/ injection | Latency (weeks) |
|---|---|---|---|---|---|
| C-3 | <1 | N.D. | 0 | 0/5 | — |
| 2-7 | <1 | N.D. | 15 | 6/6 | 2–2.5 |
| 2-1-1 | 1 | 6 | N.D. | 2/6 | 2 |
| 2-1-2 | <1 | 7 | N.D. | 6/6 | 2–3 |
| 2-5-2 | 24 | 463 | N.D. | 0/5 | — |
| 2-7-3 | 16 | 542 | 0 | 0/6 | — |
| 2-7-4 | 3 | 65 | 5 | 3/6 | 3–3.5 |

The mRNA copy number was determined by S1 mapping analysis and calculated by densitometric analysis as described previously (Fujita et al., 1987). Values given for growth in methyl cellulose gel are the means from duplicate assays. Assays for tumorigenicity are described in Experimental Procedures. N.D.: Not Done.

EXAMPLE 10

Transfection of Cells With Retrovirus Containing the Gene for IRF-1 or IRF-2

A recombinant retrovirus vector, pGDIRF2 was constructed which directs the expression of the mouse IRF-2 cDNA. The recombinant retrovirus pGDIRF2 was constructed by inserting the mouse IRF-2 cDNA into the pGD vector (Daley, G. Q. et at., Science 247: 824 (1990)). The DNA constructs were transfected in ψ2 cells (Mann, R. et al., Cell 33: 153 (1983)), resulting in the generation of supernatant with a high liter (~$10^6$ cfu/ml) of virus, as assayed by ability to confer neo-resistance to NIH3T3 cells. NIH3T3 cells were infected with the pGDIRF2 retrovirus at a high multiplicity of infection (m.o.i.) and the cells were directly subjected to the colony formation assay on methyl cellulose gel. As summarized in Table 4, the cells infected by the IRF-2 expressing virus, but not by the control pGD virus, gave rise to the formation of colonies at a high efficiency; assuming that all the cells were infected by the virus, the colony forming efficiency is similar to that of the three selected clones mentioned above (see Table 1). Recombinant retrovirus pGDIRF1 was constructed by inserting mouse IRF-1 cDNA into the pGD vector and transfected into 82 cells to generate a supernatant with high virus titer as described above for the virus pGDIRF-2. NIH3T3 cells (clones R2–7) were infected with the virus and it was found that the IRF-2 induced transformation of the cells was reversible by the introduction and increased expression of the IRF-1 gene. Consistent with this observation was a marked reduction of the colonies formed in methylcellulose gel of the R2–7 cells infected with the pGDIRF1 retrovirus (Table 5). Taken together these results show IRF-2 has an oncogenic potential, and that the maintenance of a balance between IRF-1 and IRF-2 expression is important for restrained cell growth. When this balance is perturbed by the overexpression of IRF-1, cell proliferation may be inhibited (Yamada et at., ibid; Abdollahi et al., Cell Growth and Differ. 2: 401 (1991); Kuchhoff, S. et at., Interferon Res. 12(S): 102 (1992)), whereas the overexpression of IRF-2 may promote unrestrained growth.

TABLE 4

Efficiency of Colony Formation In Methyl Cellulose Gel Following Retroviral Introduction of IRF-2 Gene

| | Efficiency of Colony Formation in Methyl Cellulose Gel (%) | |
|---|---|---|
| | pGD | pGDIRF2 |
| experiment 1 | <1, <1 | 17, 15 |
| experiment 2 | <1, <1 | 12, 16 |

TABLE 5

Colony Formation of R27 Cells Following Retroviral Induction of IRF-1 Gene

| | | Number of Colonies in Methyl Cellulose Gel Per 5000 Cells | |
|---|---|---|---|
| | m.o.i. | pGD | PGDIRF1 |
| experiment 1 | 0.3 | 417, 389 | 308, 287 |
| experiment 2 | 1 | 423, 408 | 187, 225 |
| experiment 3 | 10 | 415, 432 | 196, 124 |

DEPOSITS

The following deposits have been made at the National Institute of Bioscience and Human Technology (NIBHT; previously known as FERM), Ministry of International Trade and Industry, Yatabemachi, Tsukaba-Gun, Ibaraki, 305-Japan:

| | Accession No. | Description |
|---|---|---|
| pUCIRF-1 (deposited in E. coli JM109) | FERM BP-4416 | Contains a cDNA insert coding for human IRF-1 between restriction sites SalI (XhoI) and SmaI (HincII). A restriction map for pUCIRF-1 is depicted in FIG. 9. |
| pHIRF4S-51 (deposited in E. coli MC101) | FERM BP-4417 | Contains a cDNA insert coding for human IRF-2 between restriction sites XhoI. A restriction map of pHIRF4S-51 is depicted in FIG. 10. |
| pUCHIRF1B (deposited in E. coli HB101) | FERM BP-4424 | Contains a 19kb genomic human IRF-1 insert. See, Example 9. |

-continued

| | Accession No. | Description |
|---|---|---|
| Hybridoma TK-3 | FERM BP-4418 | Produces a monoclonal antibody TK-3 that is specific for IRF-1. See, Example 6. |

All publications mentioned hereinabove are hereby incorporated in their entirety by reference.

While the foregoing invention has been described in some detail for purposes of clarity and understanding, it will be appreciated by one skilled in the art from a reading of this disclosure that various changes in form and detail can be made without departing from the true scope of the invention and appended claims.

We claim:

1. A method of screening for leukemic tissue in a human comprising:

(a) isolating human tissue suspected of being leukemic;
   (b) determining the IRF-1/IRF-2 ratio in said tissue using nucleic acid analysis, and comparing said ratio to that of a tissue in a normal human;
   wherein the value of IRF-2 is higher than IRF-1 and the ratio in said tissue suspected of being leukemic differs from the ratio in the normal tissue is an indication of the presence of leukemic tissue.

2. A method of screening for leukemic tissue in a human comprising:

(a) isolating from a human a tissue suspected of being leukemic;
   (b) detecting loss of one or more functional IRF-1 genes from said tissue, said loss is an indication of the presence of leukemic tissue.

3. The method according to claim 2, wherein the detection of loss of said IRF-1 gene(s) comprises screening for a translocation of the gene(s) in chromosome 5.

4. The method according to claim 2, wherein the detection of loss of said IRF-1 gene(s) comprises carrying out fluorescence in situ hybridization using a labeled IRF-1 DNA probe.

5. A method of screening for leukemia in a human which comprises (a) defining a value for a parameter which is the IRF-1/IRF-2 ratio in a control sample;
   (b) removing a sample of cells from said human and subjecting the nucleic acid from said cells to an analysis to determine the value of said parameter for a cell in said sample; and
   (c) comparing the determined value from (b) with the defined value from (a) wherein the value of IRF-2 is higher than IRF-1 in said sample indicates the presence of leukemic tissue.

6. The method according to claim 5, wherein the value for IRF-1 of the parameter is the number of alleles in chromosome 5 coding for IRF-1.

7. The method according to claim 6, wherein the number of alleles in chromosome 5 coding for IRF-1 is determined by fluorescence in situ hybridization (FISH) using a labeled IRF-1 DNA probe.

8. The method according to claim 7, wherein the DNA probe is an IRF-1 cDNA probe.

9. The method according to claim 7, wherein the DNA probe is an IRF-1 genomic probe of at least 8 kb.

10. The method according to claim 5, wherein the value for IRF-1 of the parameter is the number of alleles coding for mutant IRF-1 in chromosome 5.

11. The method according to claim 5, wherein the value for IRF-1 of the parameter is the number of genes coding for IRF-1 which have been translocated in chromosome 5.

12. The method according to claim 5, wherein the value for IRF-1 of the parameter is the presence or absence of chromosome 5.

13. The method according to claim 5, wherein the parameter is determined by counting the number of IRF-1 and IRF-2 mRNA molecules per cell.

14. The method according to claim 13, wherein the number of IRF-1 and IRF-2 mRNA molecules per cell is obtained by extracting total cellular RNA from a population of cells, subjecting the extract to S1 mapping analysis using a labeled fragment of IRF-1 and IRF-2 DNA as a probe and determining the label intensity of the respective IRF-1 and IRF-2 blots.

15. The method according to claim 13, wherein the number of IRF-1 and IRF-2 mRNA molecules per cell is obtained by extracting total cellular RNA from a population of cells, subjecting the extract to RNA blotting analysis using a labeled fragment Of IRF-1 and IRF-2 DNA as a probe and determining the label intensity of the respective IRF-1 and IRF-2 blots.

* * * * *

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
        ( A ) LENGTH: 51 base pairs
        ( B ) TYPE: nucleic acid
        ( C ) STRANDEDNESS: double
        ( D ) TOPOLOGY: linear ( x i ) SEQUENCE DESCRIPTION: SEQ ID NO:1:

```
TTGTGGTAGT ACCGGTGGGG GCCCGGCAGG TTTCGCAGAT CTGCGTGCGC G         51
```

( 2 ) INFORMATION FOR SEQ ID NO:2:

( i ) SEQUENCE CHARACTERISTICS:
        ( A ) LENGTH: 51 base pairs
        ( B ) TYPE: nucleic acid
        ( C ) STRANDEDNESS: double
        ( D ) TOPOLOGY: linear ( x i ) SEQUENCE DESCRIPTION: SEQ ID NO:2:

```
ACCGGACGAG GCTGCCGGGG GCCCGGCAGG TTTCGCAGAT CTGCGTGCGC G         51
```

( 2 ) INFORMATION FOR SEQ ID NO:3:

( i ) SEQUENCE CHARACTERISTICS:
        ( A ) LENGTH: 82 base pairs
        ( B ) TYPE: nucleic acid
        ( C ) STRANDEDNESS: double
        ( D ) TOPOLOGY: linear ( x i ) SEQUENCE DESCRIPTION: SEQ ID NO:3:

```
TTCCAACCAA ATCCGGGGC TCATCTGGAT TAATAAAGTG AGTGTAACTC             50

TTTGGGTTTT CCTGCCACTG TTTAACCCA TG                                82
```

( 2 ) INFORMATION FOR SEQ ID NO:4:

( i ) SEQUENCE CHARACTERISTICS:
        ( A ) LENGTH: 82 base pairs
        ( B ) TYPE: nucleic acid (C) STRANDEDNESS: double
(D) TOPOLOGY: linear (xi) SEQUENCE DESCRIPTION: SEQ ID NO:4:

```
TTCCAACCAA ATCCCGGGGC TCATCTGGAT TAATAAAGTG AGTGTAACTC         50

TTTGGGTTTT CCTGCCACTG TTTTAACCCA TG                            82
```